United States Patent
Lietzau et al.

(10) Patent No.: US 7,514,127 B2
(45) Date of Patent: *Apr. 7, 2009

(54) DIBENZOFURAN DERIVATIVES, DIBENZOTHIOPHENE DERIVATIVES AND FLUORENE DERIVATIVES

(75) Inventors: Lars Lietzau, Darmstadt (DE); Matthias Bremer, Darmstadt (DE); Melanie Klasen-Memmer, Heuchelheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/578,376

(22) PCT Filed: Mar. 18, 2005

(86) PCT No.: PCT/EP2005/002922

§ 371 (c)(1),
(2), (4) Date: Oct. 13, 2006

(87) PCT Pub. No.: WO2005/105772

PCT Pub. Date: Nov. 10, 2005

(65) Prior Publication Data

US 2007/0219380 A1 Sep. 20, 2007

(30) Foreign Application Priority Data

Apr. 14, 2004 (DE) .................. 10 2004 018 526

(51) Int. Cl.
C09K 19/32 (2006.01)
C09K 19/34 (2006.01)
C07D 307/91 (2006.01)
C07D 333/76 (2006.01)
C07C 25/18 (2006.01)
C07C 43/225 (2006.01)

(52) U.S. Cl. .............. 428/1.1; 252/299.61; 252/299.62; 549/46; 549/47; 549/460; 570/183; 570/187; 570/188

(58) Field of Classification Search ................. 428/1.1; 252/299.61, 299.62, 299.63; 549/46, 47, 549/460; 570/183, 187, 188

See application file for complete search history.

(56) References Cited

U.S. PATENT DOCUMENTS

| 2,146,730 A | 2/1939 | Gilman et al. |
| 3,953,602 A | 4/1976 | Shemano et al. |
| 4,064,347 A | 12/1977 | Fleming et al. |
| 7,018,685 B2 * | 3/2006 | Schmidt et al. .............. 428/1.1 |
| 7,255,900 B2 * | 8/2007 | Schmidt et al. .............. 428/1.1 |
| 7,297,378 B2 * | 11/2007 | Schmidt et al. .............. 428/1.1 |

FOREIGN PATENT DOCUMENTS

| DE | 21 14 461 A1 | 10/1971 |
| DE | 19720289 | * 11/1998 |
| EP | 1 201 632 A | 5/2002 |
| EP | 1 223 209 A | 7/2002 |
| JP | 2001 064216 A | 3/2001 |
| WO | WO 02/055463 A | 7/2002 |

OTHER PUBLICATIONS

English transalation for WO 02055463, 2002.*
English transalation for EP 1223209, 2002.*
Caplus 1950: 30120.*
Caplus 1998: 787187.*
Caplus 1948: 29797.*
Caplus 2002: 99089.*

* cited by examiner

Primary Examiner—Shean C Wu
(74) Attorney, Agent, or Firm—Millen, White, Zelano, Branigan, P.C.

(57) ABSTRACT

The present invention relates to compounds of the formula I

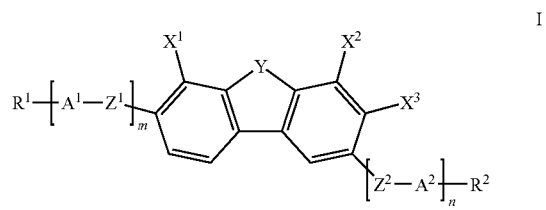

where
Y, $X^1$, $X^2$, $X^3$, $R^1$, $R^2$, $A^1$, $A^2$, $Z^1$, $Z^2$, m and n are as defined in Claim 1, to the use thereof as components in liquid-crystalline media, and to electro-optical display elements containing the liquid-crystalline media according to the invention.

15 Claims, No Drawings

DIBENZOFURAN DERIVATIVES, DIBENZOTHIOPHENE DERIVATIVES AND FLUORENE DERIVATIVES

The present invention relates to dibenzofuran, dibenzothiophene and fluorene derivatives, to liquid-crystalline media comprising these derivatives, and to electro-optical display elements containing these liquid-crystalline media. In particular, the invention relates to dibenzofuran, dibenzothiophene and fluorene derivatives of negative dielectric anisotropy.

Liquid crystals have found widespread use since the first commercially usable liquid-crystalline compounds were found about 30 years ago. Known areas of application are, in particular, displays for watches and pocket calculators, and large display panels as used in railway stations, airports and sports arenas. Further areas of application are displays of portable computers and navigation systems and video applications. For the last-mentioned applications in particular, high demands are made of the response times and contrast of the images.

The spatial arrangement of the molecules in a liquid crystal has the effect that many of its properties are direction-dependent. Of particular importance for use in liquid-crystal displays are the optical, dielectric and elasto-mechanical anisotropies. Depending on whether the molecules are oriented with their longitudinal axes perpendicular or parallel to the two plates of a capacitor, the latter has a different capacitance; in other words, the dielectric constant $\epsilon$ of the liquid-crystalline medium has different values for the two orientations. Substances whose dielectric constant is greater when the longitudinal axes of the molecules are oriented perpendicular to the capacitor plates than when they are oriented parallel are referred to as dielectrically positive. In other words, if the dielectric constant $\epsilon_\parallel$ parallel to the longitudinal axes of the molecules is greater than the dielectric constant $\epsilon_{195}$ perpendicular to the longitudinal axes of the molecules, the dielectric anisotropy $\Delta\epsilon = \epsilon_\parallel - \epsilon_{195}$ is greater than zero. Most liquid crystals used in conventional displays fall into this group.

Both the polarisability of the molecule and the permanent dipole moment play a role for the dielectric anisotropy. On application of a voltage to the display, the longitudinal axis of the molecules orients itself in such a way that the larger of the dielectric constants becomes effective. The strength of the interaction with the electric field depends on the difference between the two constants. In the case of small differences, higher switching voltages are necessary than in the case of large differences. The introduction of suitable polar groups, such as, for example, nitrile groups or fluorine, into the liquid-crystal molecules enables a broad range of working voltages to be achieved.

In the case of the liquid-crystalline molecules used in conventional liquid-crystal displays, the dipole moment oriented along the longitudinal axis of the molecules is larger than the dipole moment oriented perpendicular to the longitudinal axis of the molecules. In the most widespread TN ("twisted nematic") cells, a liquid-crystalline layer with a thickness of only from about 5 to 10 μm is arranged between two plane-parallel glass plates, onto each of which an electrically conductive, transparent layer of tin oxide or indium tin oxide (ITO) has been vapour-deposited as electrode. A likewise transparent alignment layer, usually consisting of a plastic (for example polyimides), is located between these films and the liquid-crystalline layer. This alignment layer serves to bring the longitudinal axes of the adjacent liquid-crystalline molecules into a preferential direction through surface forces in such a way that, in the voltage-free state, they lie uniformly with the same orientation, flat or with the same small tilt angle, on the inside of the display surface. Two polarisation films which only enable linear-polarised light to enter and escape are applied to the outside of the display in a certain arrangement.

By means of liquid crystals in which the larger dipole moment is oriented parallel to the longitudinal axis of the molecule, very high-performance displays have already been developed. In most cases here, mixtures of from 5 to 20 components are used in order to achieve a sufficiently broad temperature range of the mesophase and short response times and low threshold voltages. However, difficulties are still caused by the strong viewing-angle dependence in liquid-crystal displays as are used, for example, for laptops. The best imaging quality can be achieved if the surface of the display is perpendicular to the viewing direction of the observer. If the display is tilted relative to the observation direction, the imaging quality deteriorates drastically under certain circumstances. For greater comfort, attempts are being made to maximise the angle through which the display can be tilted from the viewing direction of an observer without significantly reducing the imaging quality. Attempts have recently been made to improve the viewing-angle dependence using liquid-crystalline compounds whose dipole moment perpendicular to the longitudinal axis of the molecule is larger than that parallel to the longitudinal axis of the molecule. The dielectric anisotropy $\Delta\epsilon$ is negative. In the field-free state, these molecules are oriented with their longitudinal axis perpendicular to the glass surface of the display. Application of an electric field causes them to orient themselves more or less parallel to the glass surfaces. In this way, it has been possible to achieve an improvement in the viewing-angle dependence. Displays of this type are known as VA-TFT ("vertically aligned") displays.

Development in the area of liquid-crystalline materials is still far from complete. In order to improve the properties of liquid-crystalline display elements, attempts are constantly being made to develop novel compounds which enable optimisation of such displays.

WO 02/055463 A1 discloses, inter alia, 3-monosubstituted and 3,7-disubstituted 4,6-difluorodibenzofurans and -thiophenes, without giving precise details of the physical or electro-optical properties.

It is therefore an object of the present invention to provide compounds having advantageous properties for use in liquid-crystalline media. In particular, they should have negative dielectric anisotropy, which makes them particularly suitable for use in liquid-crystalline media for VA displays.

This object is achieved in accordance with the invention by compounds of the general formula I

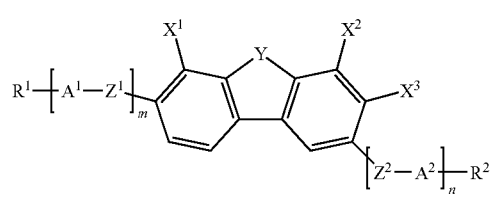

in which:

m and n are each, independently of one another, 0, 1, 2 or 3;

Y denotes O, S, S(O), $SO_2$, $CH_2$, $CF_2$, $CCl_2$, CHF, CHCl, CFCl, $C(CF_3)_2$, $CHCF_3$, $C(CN)_2$ or CHCN;

$X^1$, $X^2$ and $X^3$ each, independently of one another, denote H, halogen, CN, SCN, NCS or $SF_5$;

$A^1$ and $A^2$ each, independently of one another, denote 1,4-phenylene, in which =CH— may be replaced once or twice by =N— and which may be unsubstituted or mono- to tetrasubstituted, independently of one another, by —CN, —F, —Cl, —Br, —I, $C_1$-$C_6$-alkanyl which is unsubstituted or mono- or polysubstituted by fluorine and/or chlorine or by $C_1$-$C_6$-alkoxy which is unsubstituted or mono- or polysubstituted by fluorine and/or chlorine, 1,4-cyclohexylene, 1,4-cyclohexenylene or 1,4-cyclohexadienylene, in which —$CH_2$— may be replaced once or twice, independently of one another, by —O— or —S— in such a way that hetero atoms are not linked directly, and which may be unsubstituted or mono- or polysubstituted by —F, —Cl, —Br and/or —I;

$Z^1$ and $Z^2$ each, independently of one another, denote a single bond, a double bond, —$CF_2O$—, —$OCF_2$—, —$CH_2CH_2$—, —$CF_2CF_2$—, —$CF_2CH_2$—, —$CH_2CF_2$—, —CHF—CHF—, —C(O)O—, —OC(O)—, —$CH_2O$—, —$OCH_2$—, —CF=CH—, —CH=CF—, —CF=CF—, —CH=CH— or —C≡C—;

$R^1$ and $R^2$ denote hydrogen, an alkanyl, alkoxy, alkenyl or alkynyl radical having 1 to 15 or 2 to 15 C atoms respectively which is unsubstituted, monosubstituted by —CN or —$CF_3$ or monosubstituted or polysubstituted by —F, —Cl, —Br and/or —I, where, in addition, one or more $CH_2$ groups in these radicals may each, independently of one another, be replaced by —O—, —S—, —$SO_2$—, —CO—, —COO—, —OCO— or —O—CO—O— in such a way that hetero atoms are not linked directly, —F, —Cl, —Br, —I, —CN, —SCN, —NCS or —$SF_5$;

where $A^1$, $A^2$, $Z^1$, $Z^2$, $R^1$ and $R^2$ may each have identical or different meanings if m or n is greater than 1;

and where, in the case where simultaneously n=0, $X^1$ denotes F, $X^2$ denotes H or F and $X^3$ denotes H, $R^2$ then does not denote H.

The compounds have negative Δε and are therefore suitable, in particular, for use in VA-TFT displays. The compounds according to the invention preferably have a Δε of <−2 and particularly preferably a Δε of <−4. They exhibit very good compatibility with the usual substances used in liquid-crystal mixtures for displays.

Furthermore, the compounds of the formula I according to the invention have values for the optical anisotropy Δn which are particularly suitable for use in VA-TFT displays. The compounds according to the invention preferably have a Δn of greater than 0.05 and less than 0.40.

The other physical, physicochemical or electro-optical parameters of the compounds according to the invention are also advantageous for use of the compounds in liquid-crystalline media. The compounds or liquid-crystalline media comprising these compounds have, in particular, a sufficient breadth of the nematic phase and good low-temperature and long-term stability as well as sufficiently high clearing points.

It is preferred for Y to stand for oxygen, sulfur, $CH_2$, $CCl_2$ or $CF_2$; in particular Y is an oxygen atom or $CF_2$.

It is furthermore preferred for at least one of the radicals $X^1$, $X^2$ and $X^3$ to denote halogen. Particularly preferably, at least two of the substituents $X^1$, $X^2$ and $X^3$ denote halogen and the third denotes hydrogen or halogen. Very particularly preferably, all three radicals $X^1$, $X^2$ and $X^3$ are halogen. Halogen here is in particular fluorine.

$A^1$ and $A^2$ are preferably and independently of one another an optionally substituted 1,4-phenylene, an optionally substituted 1,4-cyclohexylene, in which —$CH_2$— may be replaced once or twice by —O—, or an optionally substituted 1,4-cyclohexenylene. If n or m is 2 or 3, the rings $A^1$ and $A^2$ may adopt identical or different meanings.

$A^1$ and $A^2$ are particularly preferably, independently of one another,

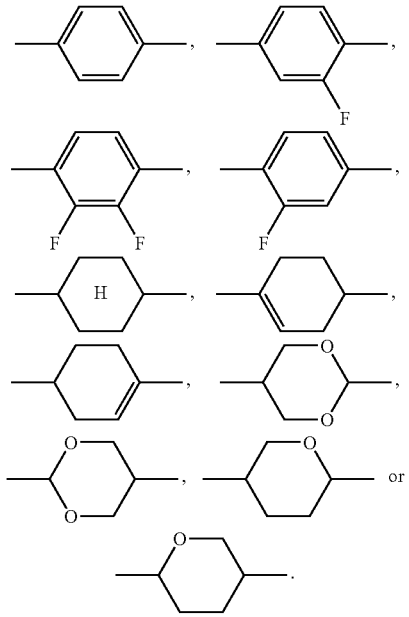

$A^1$ and $A^2$ are very particularly preferably 1,4-cyclohexylene rings and/or optionally fluorine-substituted 1,4-phenylene rings.

$Z^1$ and $Z^2$ are preferably, independently of one another, a single bond, —$CH_2O$—, —$OCH_2$—, —$CF_2O$—, —$OCF_2$—, —$CF_2CF_2$—, —CH=CH—, —CF=CH—, —CH=CF— or —CF=CF—, particularly preferably, independently of one another, a single bond, —$CF_2O$—, —$OCF_2$—, —$CF_2CF_2$—, —CH=CH—, —CF=CH—, —CH=CF— or —CF=CF—. $Z^1$ and $Z^2$ are very particularly preferably, independently of one another, a single bond, —$CF_2O$—, —$OCF_2$—, —$CF_2CF_2$— or —CF=CF—.

If $R^1$ and $R^2$ in the formula I each, independently of one another, represent an alkanyl radical and/or an alkoxy radical (alkyloxy radical) having 1 to 15 C atoms which is straight-chain or branched. Each of these radicals is preferably straight-chain, has 1, 2, 3, 4, 5, 6 or 7 C atoms and is accordingly preferably methyl, ethyl, propyl, butyl, pentyl, hexyl, heptyl, methoxy, ethoxy, propoxy, butoxy, pentoxy, hexoxy or heptoxy.

$R^1$ and $R^2$ in the formula I may each, independently of one another, also be an oxaalkyl radical, i.e. an alkanyl radical in which at least one of the non-terminal $CH_2$ groups has been replaced by —O—, preferably straight-chain 2-oxapropyl (=methoxymethyl), 2-(=ethoxymethyl) or 3-oxabutyl (=methoxyethyl), 2-, 3- or 4-oxapentyl, 2-, 3-, 4- or 5-oxahexyl, 2-, 3-, 4-, 5- or 6-oxaheptyl. In a corresponding manner, $R^1$ and $R^2$ in the formula I may also, independently of one another, be thioalkanyl or sulfonealkanyl radicals, i.e. alkanyl radicals in which one $CH_2$ group has been replaced by —S— or —$SO_2$—.

$R^1$ and $R^2$ in the formula I may furthermore each, independently of one another, be an alkenyl radical having 2 to 15 C atoms which is straight-chain or branched and has at least one C—C double bond. It is preferably straight-chain and has 2 to 7 C atoms. Accordingly, it is preferably vinyl, prop-1- or -2-phenyl, but-1-, -2- or -3-phenyl, pent-1-, -2-, -3- or -4-phenyl, hex-1-, -2-, -3-, -4- or -5-phenyl, or hept-1-, -2-, -3-, -4-, -5- or -6-phenyl. If the two C atoms of the C—C double bond are substituted, the alkenyl radical can be in the form of the E and/or Z isomer (trans/cis). In general, the respective E isomers are preferred.

In the same way as for an alkanyl radical, at least one of the $CH_2$ groups in an alkenyl radical may also be replaced by oxygen, sulfur or —$SO_2$—. In the case of replacement by —O—, an alkenyloxy radical (having a terminal oxygen) or an oxaalkenyl radical (having a non-terminal oxygen) is then present.

$R^1$ and $R^2$ in the formula I may also, independently of one another, be an alkynyl radical having 2 to 15 C atoms which is straight-chain or branched and has at least one C—C triple bond.

$R^1$ and $R^2$ in the formula I may each, independently of one another, be an alkanyl radical having 1 to 15 C atoms in which one $CH_2$ group has been replaced by —O— and one has been replaced by —CO—, these preferably being adjacent. This thus contains an acyloxy group —CO—O— or an oxycarbonyl group —O—CO—. This radical is preferably straight-chain and has 2 to 6 C atoms. The following of these radicals are preferred here: acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 2-acetoxypropyl, 3-propionyloxy-propyl, 4-acetoxybutyl, methoxycarbonyl, ethoxycarbonyl, propoxycarbonyl, butoxycarbonyl, pentoxycarbonyl, methoxycarbonylmethyl, ethoxycarbonyl-methyl, propoxycarbonylmethyl, butoxycarbonylmethyl, 2-(methoxy-carbonyl)ethyl, 2-(ethoxycarbonyl)ethyl, 2-(propoxycarbonyl)ethyl, 3-(methoxycarbonyl)propyl, 3-(ethoxycarbonyl)propyl and 4-(methoxy-carbonyl)butyl. Furthermore, an alkanyl radical can also have an —O—CO—O— unit. Replacement of a $CH_2$ group by only one —CO— group (carbonyl function) is also possible.

$R^1$ and $R^2$ in the formula I may each, independently of one another, be an alkenyl radical having 2 to 15 C atoms in which a $CH_2$ group, preferably in the vicinity of an unsubstituted or substituted —C≡C— unit, has been replaced by —CO—, —CO—O—, —O—CO— or —O—CO—O—, where this radical may be straight-chain or branched. The radical is preferably straight-chain and has 4 to 13 C atoms. Particular preference is given here to acryloyloxymethyl, 2-acryloyloxyethyl, 3-acryloyloxypropyl, 4-acryloyloxybutyl, 5-acryloyloxy-pentyl, 6-acryloyloxyhexyl, 7-acryloyloxyheptyl, 8-acryloyloxyoctyl, 9-acryloyloxynonyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl AND 8-methacryloyloxy-octyl. Correspondingly, a $CH_2$ group in the vicinity of a substituted —C≡C— unit in an alkynyl radical may also be replaced by —CO—, —CO—O—, —O—CO— or —O—CO—O—.

$R^1$ and $R^2$ in the formula I may each, independently of one another, be an alkanyl radical or alkoxy radical having 1 to 15 C atoms or an alkenyl radical or alkynyl radical having 2 to 15 C atoms, each of which is monosubstituted by —CN or —$CF_3$, where these are preferably straight-chain. The substitution by —CN or —$CF_3$ is possible in any desired position.

$R^1$ and $R^2$ in the formula I may each, independently of one another, be an alkanyl radical in which two or more $CH_2$ groups have been replaced by —O— and/or —CO—O—, where this may be straight-chain or branched. It is preferably branched and has 3 to 12 C atoms.

$R^1$ and $R^2$ in the formula I may each, independently of one another, be an alkanyl radical or alkoxy radical having 1 to 15 C atoms or an alkenyl radical or alkynyl radical having 2 to 15 C atoms, each of which is monosubstituted or polysubstituted by F, Cl, Br and/or I, where these radicals are preferably straight-chain and halogen is preferably —F and/or —Cl. In the case of polysubstitution, halogen is preferably —F. The resultant radicals also include perfluorinated radicals, such as —$CF_3$. In the case of mono-substitution, the fluorine or chlorine substituent can be in any desired position, but is preferably in the ω position.

$R^1$ and $R^2$ in the formula I may also each, independently of one another, be —F, —Cl, —Br, —I, —CN, —SCN, —NCS or —$SF_5$.

$R^1$ and $R^2$ in the general formula I are particularly preferably, independently of one another, hydrogen or an alkanyl radical, alkoxy radical or alkenyl radical having 1 to 7 or 2 to 7 C atoms respectively, where each of these radicals is preferably unsubstituted or monosubstituted or polysubstituted by halogen.

In connection with the present invention, halogen denotes fluorine, chlorine, bromine or iodine.

In connection with the present invention, the term "alkyl"—unless defined otherwise elsewhere in this description or in the claims—denotes a straight-chain or branched aliphatic hydrocarbon radical having 1 to 15 (i.e. 1, 2, 3, 4, 5, 6, 7, 8, 9, 10, 11, 12, 13, 14 or 15) carbon atoms. This radical is unsubstituted or monosubstituted or polysubstituted by fluorine, chlorine, bromine, iodine, carboxyl, nitro, —$NH_2$, —N(alkanyl)$_2$ and/or cyano, where the polysubstitution can take place with identical or different substituents. If this alkyl radical is a saturated radical, it is also referred to as "alkanyl". Furthermore, the term "alkyl" also encompasses hydrocarbon radicals which are unsubstituted or correspondingly mono- or polysubstituted by identical or different substituents, in particular by —F, —Cl, —Br, —I and/or —CN or —$CF_3$, and in which one or more $CH_2$ groups may be replaced by —O— ("alkoxy", "oxaalkyl"), —S— ("thioalkyl"), —$SO_2$—, —CH═CH— ("alkenyl"), —C≡C— ("alkynyl"), —CO—O—, —O—CO— or —O—CO—O— in such a way that hetero atoms (O or S) in the chain are not linked directly to one another.

Preferred compounds of the general formula I have a total of zero, one, two or three units -$Z^1$-$A^1$- and/or -$Z^2$-$A^2$-, i.e. m+n=0, 1, 2 or 3 where m and n are each 0, 1, 2 or 3. If two or three units -$Z^1$-$A^1$- and/or -$Z^2$-$A^2$- are present, they may be bonded to only one side of the molecule (i.e. m=2 or 3 and n=0 or n=2 or 3 and m=0) or also to both sides of the molecule. Particularly preferably, m+n=0, 1 or 2.

Preferred compounds of the formula I for which m+n=0 are represented by the following formula:

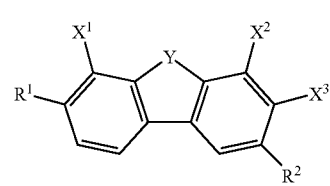

Ia in which $R^1$, $R^2$, $X^1$, $X^2$, $X^3$ and Y have the same and the same preferred meanings as defined above for the formula I. In particular, Y stands for an oxygen atom or a $CF_2$ group.

Preferred compounds of the formula I for which m+n=1 are represented by the following formulae:

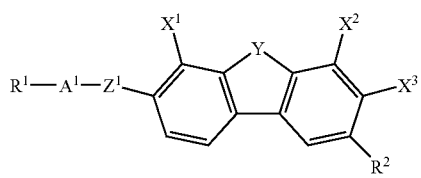
Ib

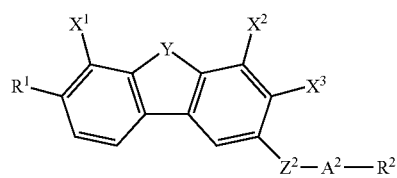
Ic in which $R^1$, $R^2$, $A^1$, $A^2$, $X^1$, $X^2$, $X^3$, $Z^1$, $Z^2$ and Y have the same and the same preferred meanings as defined above for the formula I. In particular, Y stands for an oxygen atom or a $CF_2$ group.

Preferred compounds of the formula I for which m+n=2 are represented by the following formulae:

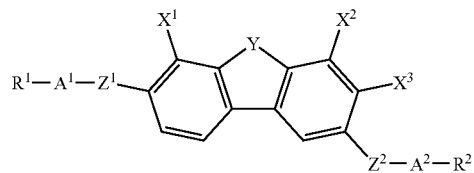
Id

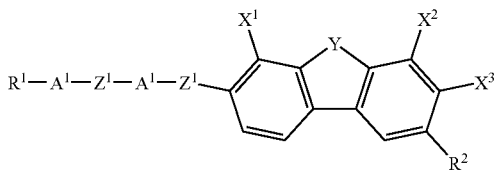
Ie

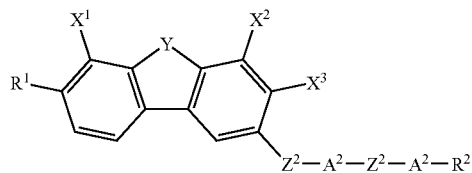
If in which $R^1$, $R^2$, $A^1$, $A^2$, $X^1$, $X^2$, $X^3$, $Z^1$, $Z^2$ and Y have the same and the same preferred meanings as defined above for the formula I. If $A^1$, $A^2$, $Z^1$ or $Z^2$ occurs twice in the formulae Ie and If, they can in each case have identical or different meanings. In particular, Y stands for an oxygen atom or a $CF_2$ group.

Preferred compounds of the formula I for which m+n=3 are represented by the following formulae:

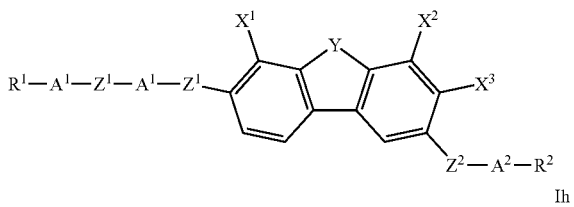
Ig

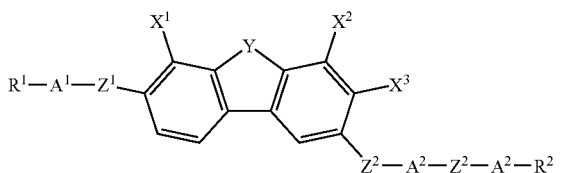
Ih

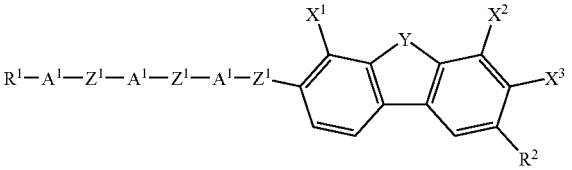
Ii

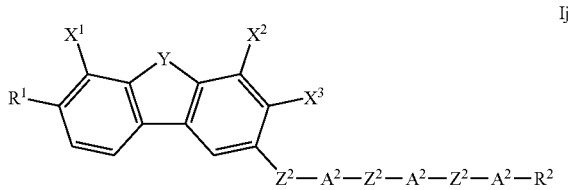
Ij in which $R^1$, $R^2$, $A^1$, $A^2$, $X^1$, $X^2$, $X^3$, $Z^1$, $Z^2$ and Y have the same and the same preferred meanings as defined above for the formula I. If $A^1$, $A^2$, $Z^1$ or $Z^2$ occurs more than once in the formulae Ig to Ij, they can in each case have identical or different meanings. In particular, Y stands for an oxygen atom or a $CF_2$ group.

Particular preference is given to compounds of the formulae Ia, Ib, Ic and Id according to the invention, in particular of the formulae Ia, Ib and Id.

Very particularly preferred compounds of the formula Ia are the following:

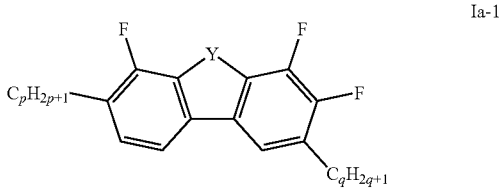
Ia-1

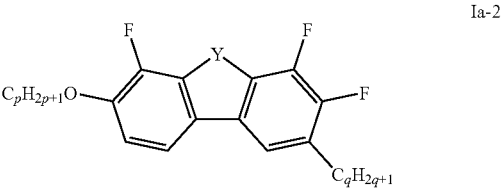
Ia-2

-continued

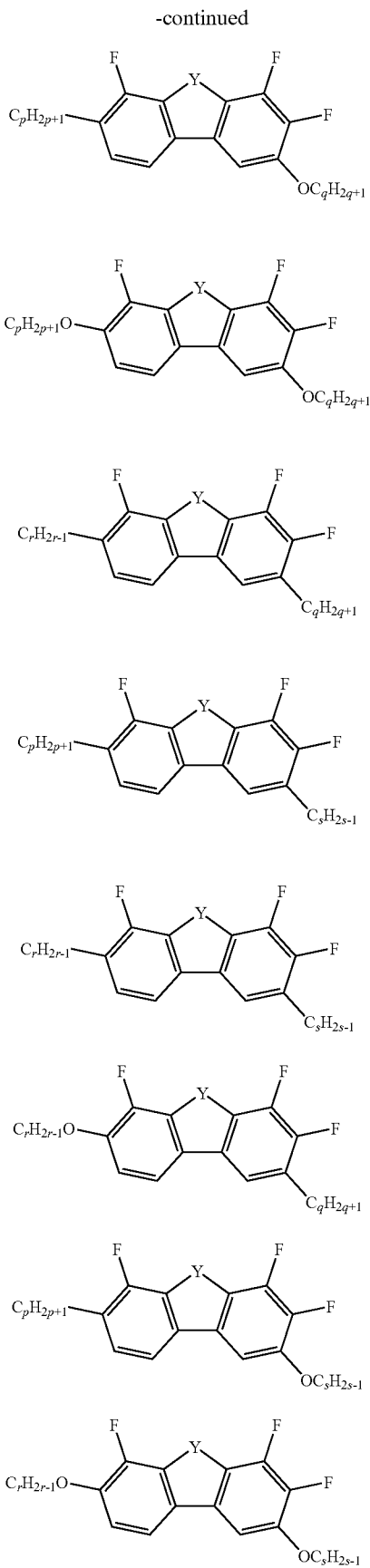

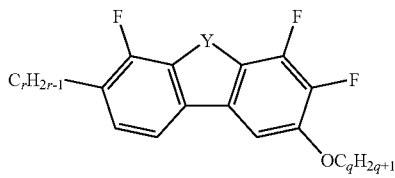

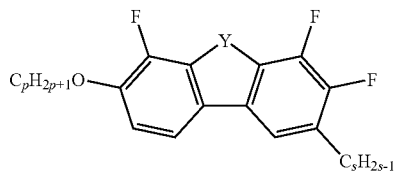

in which p and q are each, independently of one another, 1, 2, 3, 4, 5, 6, 7 or 8, and r and s are each, independently of one another, 2, 3, 4, 5, 6, 7 or 8, where the respective radicals are preferably straight-chain and one to four of the hydrogen atoms in each of the radicals may be replaced by fluorine, and Y stands for an oxygen atom or a $CF_2$ group. Of the compounds of the formulae Ia-1 to Ia-12, those of the formulae Ia-1 to Ia-7 are still further preferred, in particular compounds of the formula Ia-1.

Of the preferred compounds of the formula Ib according to the invention, particular preference is given to the following:

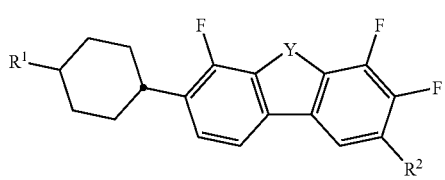

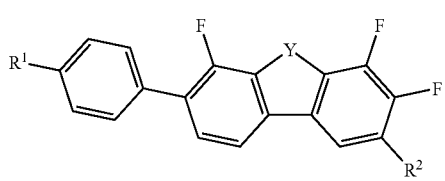

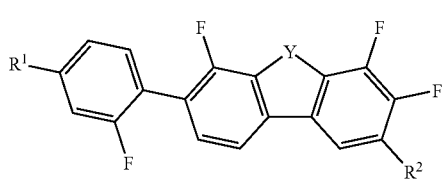

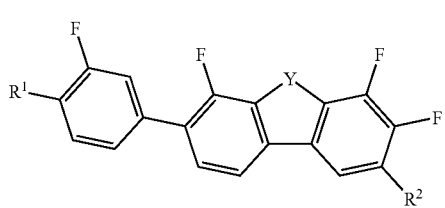

Ib-5
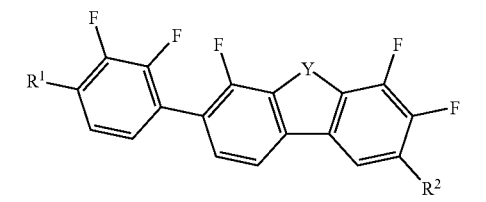

Ib-6
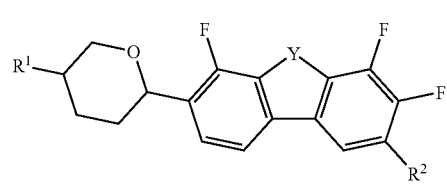

Ib-7
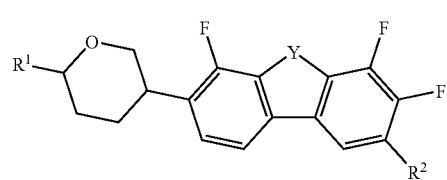

Ib-8
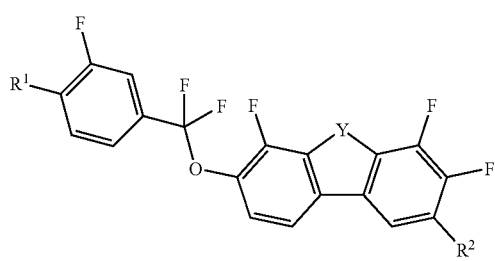

Ib-9
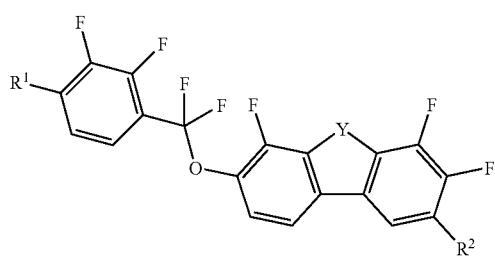

Ib-10
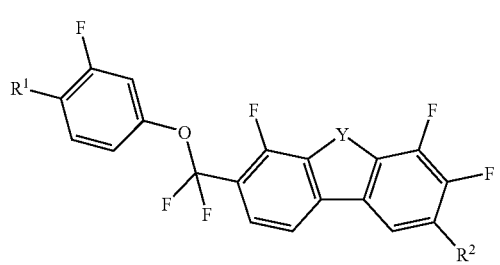

Ib-11
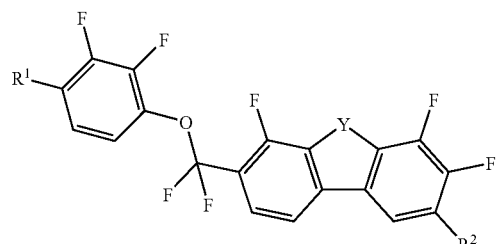

Ib-12
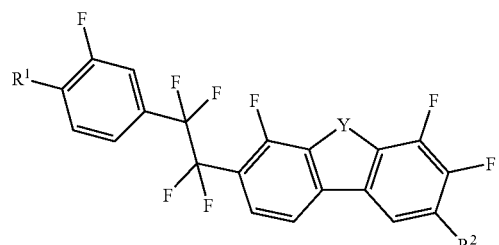

Ib-13
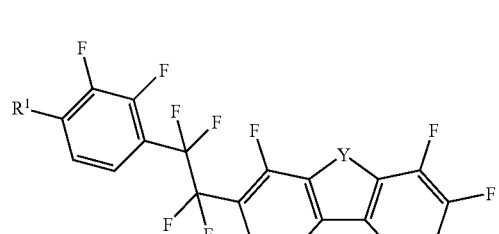

Ib-14
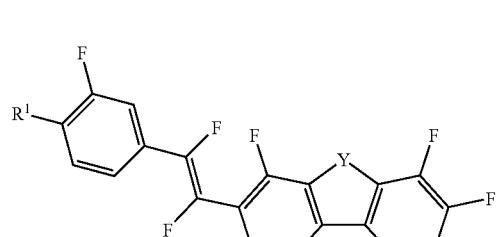

Ib-15
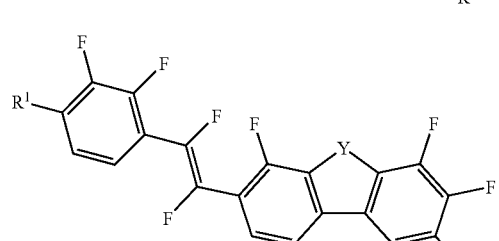

in which $R^1$, $R^2$ and Y have the same and the same preferred meanings as defined above for the formula I. Very particularly preferably, $R^1$ is an alkanyl radical, alkoxy radical or alkenyl radical having 1 to 7 or 2 to 7 carbon atoms respectively, $R^2$ is hydrogen or an alkanyl radical, alkoxy radical or alkenyl radical having 1 to 7 or 2 to 7 carbon atoms respectively, and Y is an oxygen atom or a $CF_2$ group.

Of the preferred compounds of the formula Id according to the invention, particular preference is given to the following:

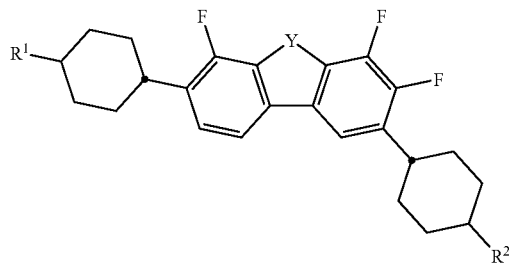
Id-1

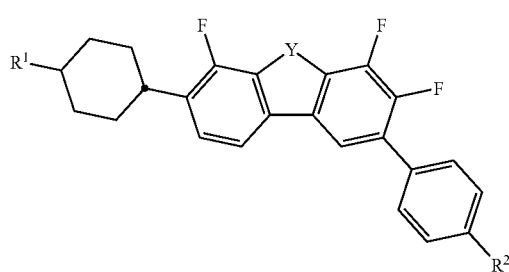
Id-2

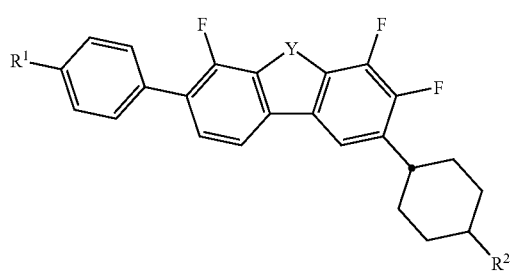
Id-3

Id-4

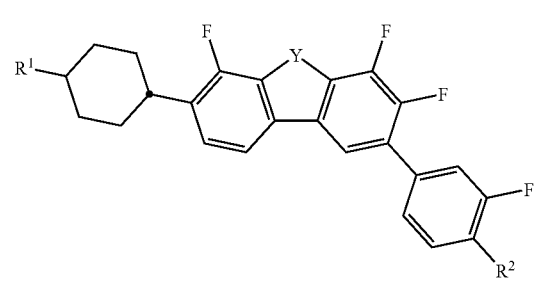
Id-5

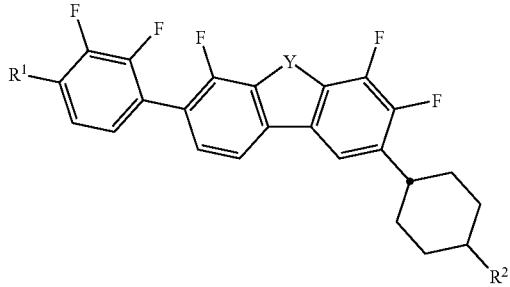
Id-6

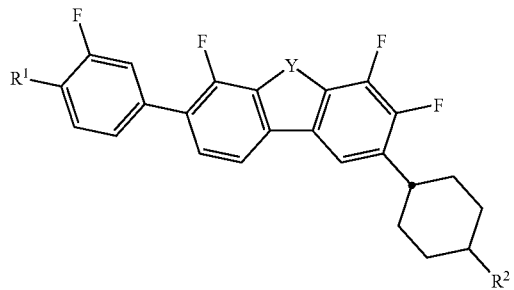

in which $R^1$, $R^2$ and Y have the same and the same preferred meanings as defined above for the formula I. Very particularly preferably, $R^1$ is an alkanyl radical, alkoxy radical or alkenyl radical having 1 to 7 or 2 to 7 carbon atoms respectively, $R^2$ is hydrogen or an alkanyl radical, alkoxy radical or alkenyl radical having 1 to 7 or 2 to 7 carbon atoms respectively, and Y is an oxygen atom or a $CF_2$ group. Of the compounds of the formulae Id-1 to Id-6, compounds of the formula Id-1 are the most preferred.

If radicals or substituents of the compounds according to the invention or the compounds according to the invention themselves exist as optically active or stereoisomeric radicals, substituents or compounds respectively since they have, for example, a centre of asymmetry, these are also encompassed by the present invention. It goes without saying here that the compounds of the general formula I according to the invention can exist in isomerically pure form, for example as pure enantiomers, diastereomers, E or Z isomers, trans or cis isomers, or as a mixture of a plurality of isomers in any desired ratio, for example as a racemate, E/Z isomer mixture or cis/trans isomer mixture.

The compounds of the general formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can be made here of variants which are known per se, but are not mentioned here in greater detail.

If desired, the starting materials can also be formed in situ by not isolating them from the reaction mixture, but instead immediately converting them further into the compounds of the general formula I.

The syntheses of various compounds of the general formula I according to the invention are described by way of example in the examples. The starting substances are obtainable by generally accessible literature procedures or are commercially available. The reactions described should be regarded as known from the literature.

The illustrative synthesis of a dibenzofuran according to the invention (Y=O, $X^1$, $X^2$ and $X^3$=F, m and n=0, and $R^1$ and $R^2$=n-propyl) is shown below. The synthesis can be adapted to the compounds of the general formula I respectively desired through the choice of suitable starting materials. The individual synthesis steps should likewise be regarded as known from the literature.

Synthesis of the Boronic Acid 4:

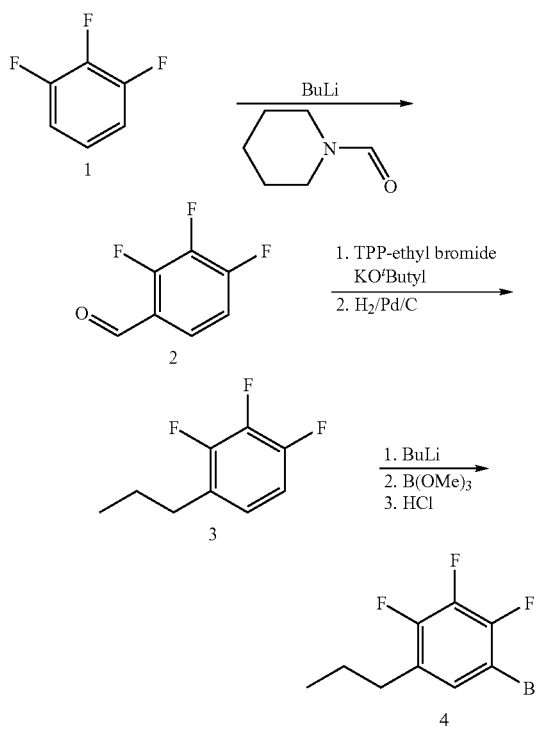

Trifluorobenzene 1 is converted into the aldehyde 2 using butyllithium and N-formylpiperidine. After the subsequent Wittig reaction, a hydrogenation on a palladium catalyst is carried out. The trifluoropropylbenzene 3 is converted into the boronic acid 4 under standard conditions.

Synthesis of the Silyl Ether 8:

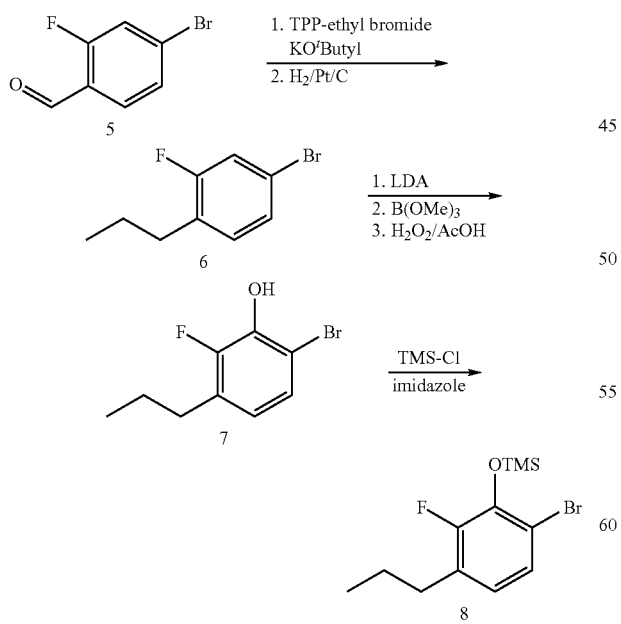

The aldehyde 5 is converted into the bromofluoropropylbenzene 6 by means of a Wittig reaction and subsequent hydrogenation on a platinum catalyst. The boronic acid ester obtained from lithium diisopropylamide (LDA) and trimethyl borate is converted into the phenol 7 analogously to a hydroboration. The OH function is converted into the silyl ether 8 using trimethylsilyl chloride (TMS-Cl) and imidazole.

Synthesis of the Dibenzofuran:

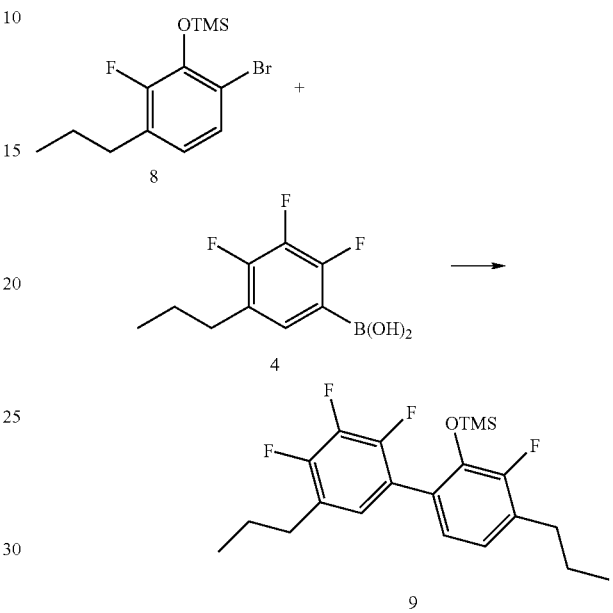

The silyl ether 8 is dissolved in toluene under nitrogen, and sodium carbonate, water and tetrakis(triphenylphosphine) palladium are added. A solution of the boronic acid 4 in absolute ethanol is slowly added to the reaction mixture at the boiling temperature. After boiling under reflux and cooling, the phases are separated. The aqueous phase is extracted with MTB ether. The organic phase is dried over sodium sulfate and evaporated. The residue is chromatographed on silica gel.

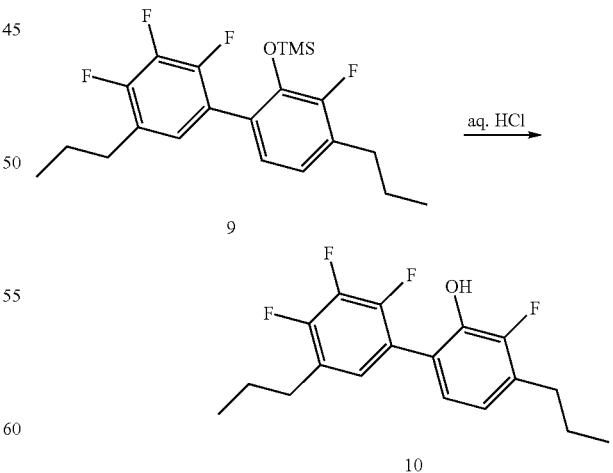

The silyl ether 9 is dissolved in THF, and dil. HCl is added. The solution is stirred at room temperature until conversion is complete. The solvent is subsequently removed, and the residue is taken up in dil. HCl solution and MTB ether. The aqueous phase is extracted three times with MTB ether. The organic phase is dried, evaporated and passed through silica gel.

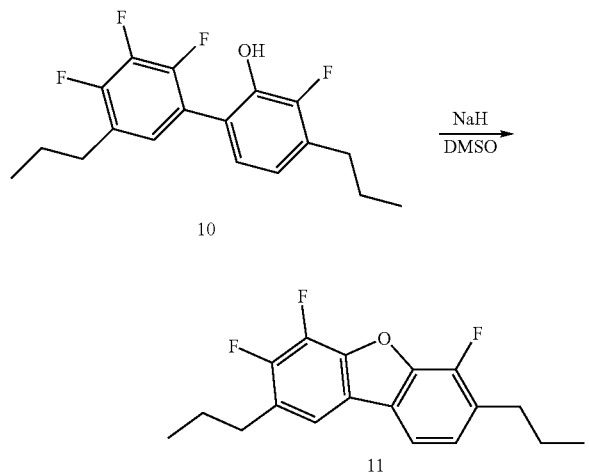

10

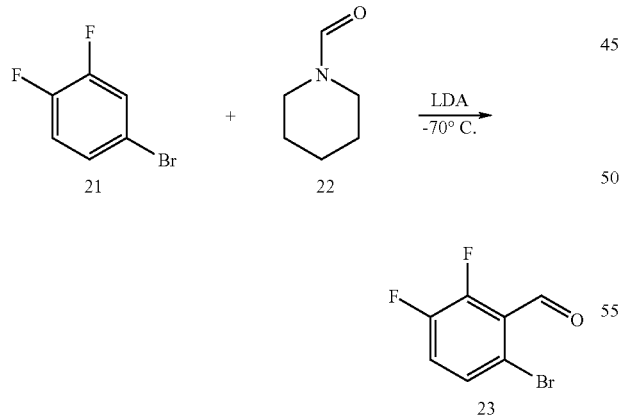

11

The phenol 10 is dissolved in DMSO under nitrogen, a 60% sodium hydride/mineral oil suspension is added, and the mixture is warmed to 120° C. After 5 hours at this temperature, the cooled batch is added to dil. HCl solution. The aqueous phase is extracted with MTB ether. The organic phase is dried over sodium sulfate, evaporated and chromatographed on silica gel.

The illustrative synthesis of a fluorene derivative according to the invention (Y=CF$_2$, X$^1$, X$^2$ and X$^3$=F, m and n=0 and R$^1$=ethoxy, R$^2$=n-propyl) is shown below. The synthesis can be adapted to the compounds of the general formula I respectively desired through the choice of suitable starting materials. The individual synthesis steps should likewise be regarded as known from the literature.

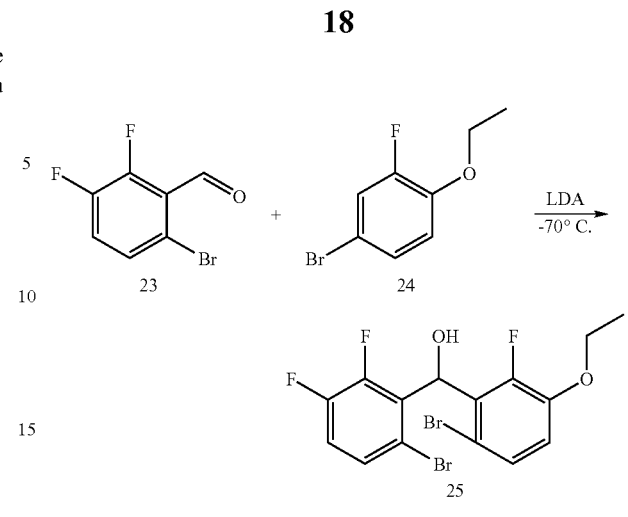

A 2M solution of lithium diisopropylamide in cyclohexane/ethylbenzene/THF is added under nitrogen and at −70° C. to a solution of the aromatic compound 21 in THF. N-Formylpiperidine 22 is added to the batch. The batch is hydrolysed at 0° C. and acidified using hydrochloric acid. Work-up gives the aldehyde 23.

A 2M solution of lithium diisopropylamide in cyclohexane/ethylbenzene/THF is added under nitrogen and at −70° C. to a solution of the aromatic compound 24 in THF. The aldehyde 23, dissolved in THF, is added to the batch. The batch is hydrolysed and acidified using hydrochloric acid. Work-up gives the diphenylmethanol 25.

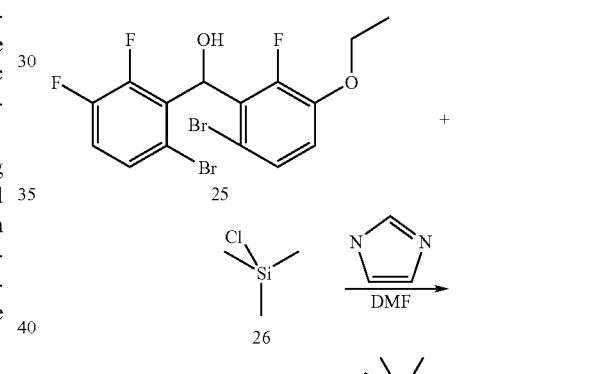

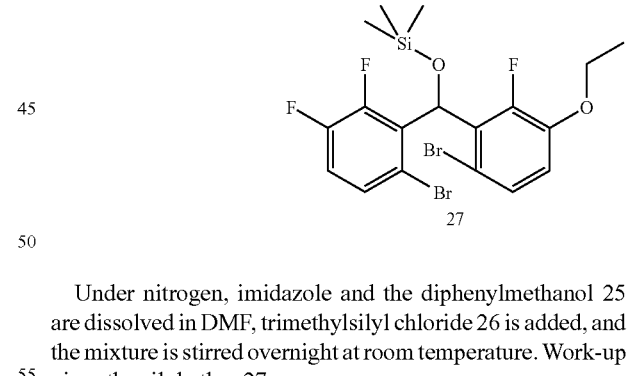

Under nitrogen, imidazole and the diphenylmethanol 25 are dissolved in DMF, trimethylsilyl chloride 26 is added, and the mixture is stirred overnight at room temperature. Work-up gives the silyl ether 27.

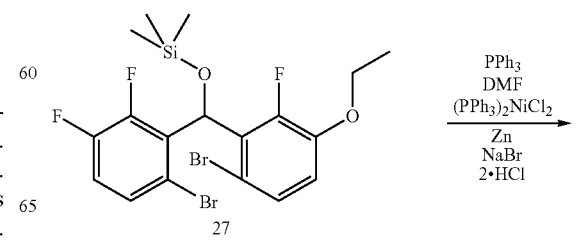

-continued

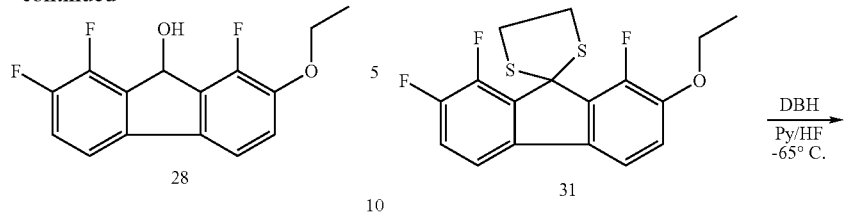

DMF is added under nitrogen to zinc, bistriphenylphosphinenickel(II) chloride, sodium bromide and triphenylphosphine, and the mixture is warmed to 80° C. After 30 minutes, the silyl ether 27, dissolved in DMF, is added dropwise to the batch. Work-up gives the fluorenol 28.

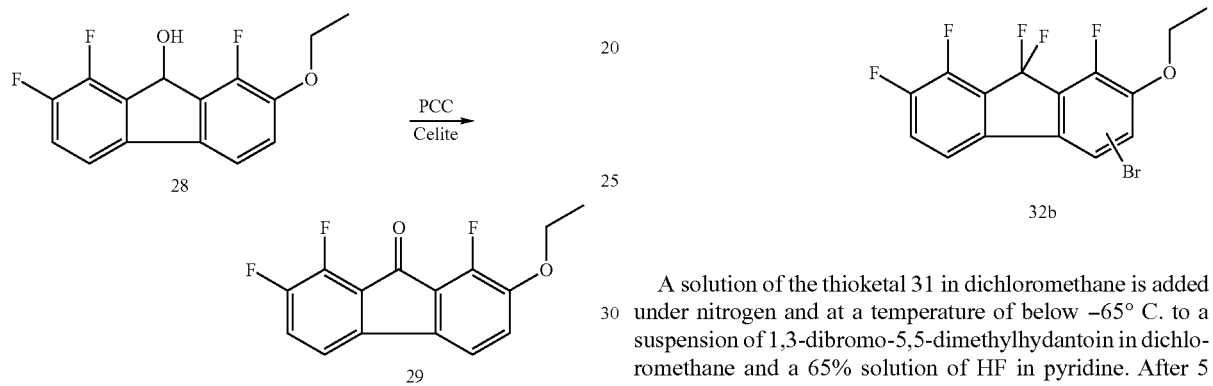

Pyridinium chlorochromate (PCC) is added under nitrogen to a suspension of Celite in dichloromethane. A solution of the fluorenol 28 in dichloromethane is subsequently added to the suspension. The batch is stirred overnight at room temperature. Work-up gives the fluorenone 29.

Boron trifluoride/diethyl ether complex is added under nitrogen and at −10° C. to a solution of the fluorenone 29 and ethanedithiol 30 in dichloromethane. The batch thaws overnight and is carefully added to sat. sodium hydrogencarbonate solution. The pH is adjusted to 8. Work-up gives the thioketal 31.

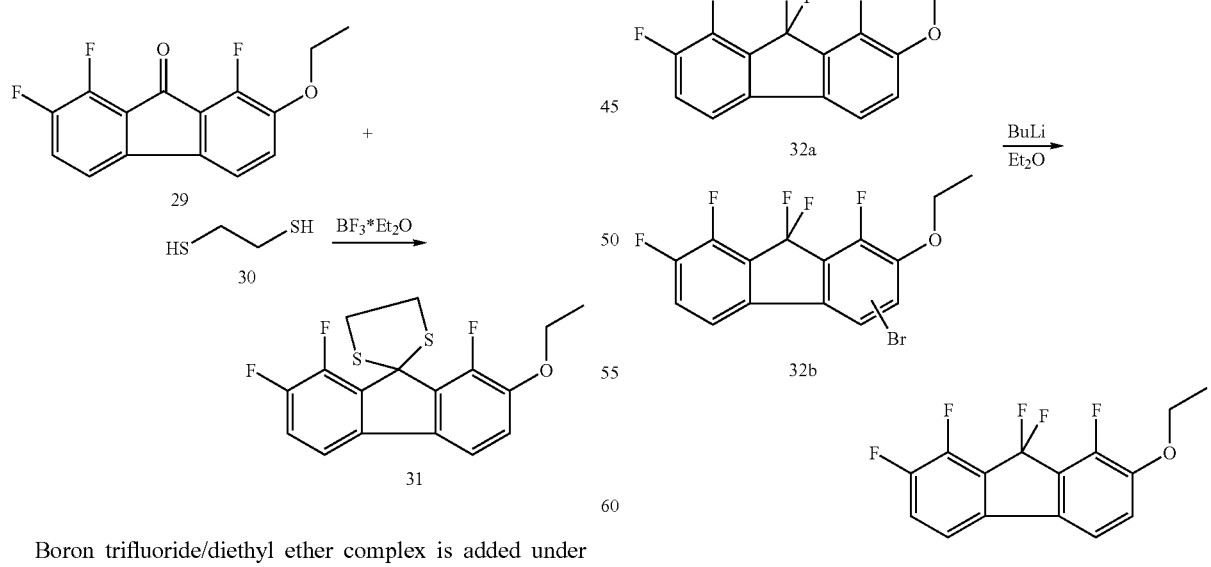

A solution of the thioketal 31 in dichloromethane is added under nitrogen and at a temperature of below −65° C. to a suspension of 1,3-dibromo-5,5-dimethylhydantoin in dichloromethane and a 65% solution of HF in pyridine. After 5 hours, the cooling is removed, and the batch is stirred overnight. The batch is subsequently added to ice-cooled 1N sodium hydroxide solution to which 19% sodium hydrogensulfite solution has been added. The pH is adjusted to 8. Work-up gives a mixture of the fluorenes 32a and 32b.

The fluorene mixture is dissolved in diethyl ether under nitrogen, and a 15% solution of butyllithium in n-hexane is added at −70° C. After 1 hour, a 1:1 THF/water mixture is added to the solution, and the batch is warmed to room temperature. Work-up gives the fluorene 32a.

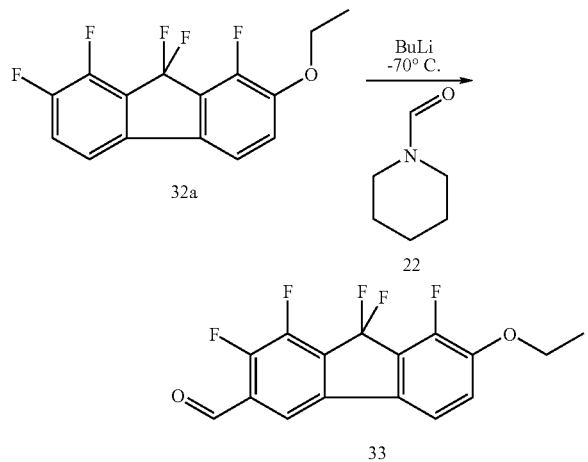

A 15% solution of butyllithium in n-hexane is added under nitrogen and at −70° C. to a solution of the fluorene 32a in THF. N-Formylpiperidine 22 is added to the batch. The batch is hydrolysed and acidified using hydrochloric acid. Work-up gives the aldehyde 33.

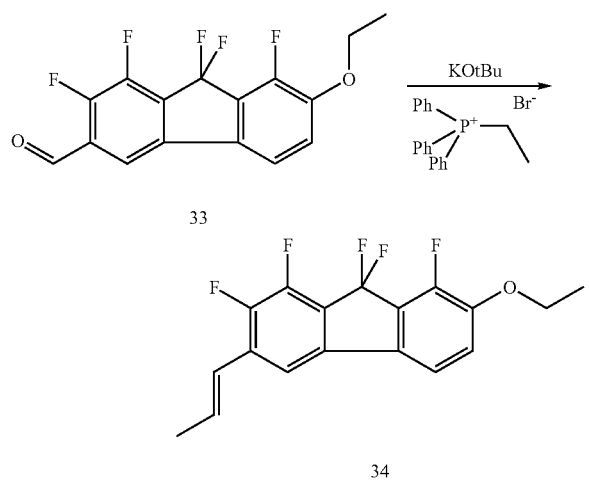

A solution of potassium tert-butoxide in THF is added under nitrogen to a suspension of ethyltristriphenylphosphonium bromide in THF at 0° C. After 1 hour, the aldehyde 33, dissolved in THF, is slowly added. The batch is stirred overnight at room temperature, and water is subsequently added. Work-up gives the olefin 34.

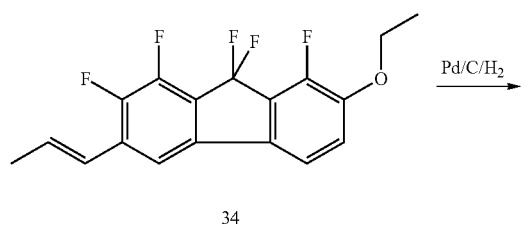

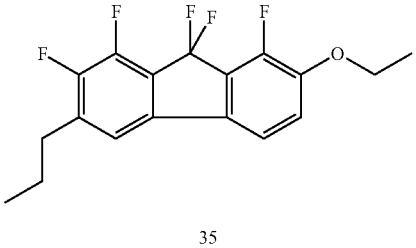

The olefin 34 is dissolved in THF and hydrogenated on a palladium catalyst. The hydrogenation solution is evaporated. Work-up gives the pentafluorofluorene 35.

The reaction schemes shown should only be regarded as illustrative. The person skilled in the art can carry out corresponding variations of the syntheses described and also follow other suitable synthetic routes in order to obtain compounds of the formula I.

As already mentioned, the compounds of the general formula I can be used in liquid-crystalline media.

The present invention therefore also relates to a liquid-crystalline medium comprising at least two liquid-crystalline compounds, comprising at least one compound of the general formula I.

The present invention also relates to liquid-crystalline media comprising from 2 to 40, preferably from 4 to 30, components as further constituents besides one or more compounds of the formula I according to the invention. These media particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, 1,3-dioxanes, 2,5-tetrahydropyrans, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4',4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexyl-ethanes, 1-phenyl-2-cyclohexylethanes, 1-cyclohexyl-2-(4-phenylcyclohexyl) ethanes, 1-cyclohexyl-2-biphenylethanes, 1-phenyl-2-cyclohexyl-phenylethanes, optionally halogenated stilbenes, benzyl phenyl ethers, tolans and substituted cinnamic acids. The 1,4-phenylene groups in these compounds may also be mono- or polyfluorinated.

The most important compounds suitable as further constituents of media according to the invention can be characterised by the formulae (II), (III), (IV), (V) and (VI):

| | |
|---|---|
| R'-L-E-R" | (II) |
| R'-L-COO-E-R" | (III) |
| R'-L-OOC-E-R" | (IV) |
| R'-L-CH$_2$CH$_2$-E-R" | (V) |
| R'-L-CF$_2$O-E-R" | (VI) |

In the formulae (II), (III), (IV), (V) and (VI), L and E, which may be identical or different, each, independently of one another, denote a divalent radical from the group formed by -Phe-, -Cyc-, -Phe-Phe-, -Phe-Cyc-, -Cyc-Cyc-, -Pyr-, -Dio-, -Thp-, -G-Phe- and -G-Cyc- and their mirror images, where Phe denotes unsubstituted or fluorine-substituted 1,4-phenylene, Cyc denotes trans-1,4-cyclohexylene or 1,4-cyclohexenylene, Pyr denotes pyrimidine-2,5-diyl or pyridine-2,5-diyl, Dio denotes 1,3-dioxane-2,5-diyl, Thp denotes tetrahydropyran-2,5-diyl and G denotes 2-(trans-1,4-cyclohexyl)ethyl, pyrimidine-2,5-diyl, pyridine-2,5-diyl, 1,3-dioxane-2,5-diyl or tetrahydropyran-2,5-diyl.

One of the radicals L and E is preferably Cyc or Phe. E is preferably Cyc, Phe or Phe-Cyc. The media according to the invention preferably comprise one or more components selected from the compounds of the formulae (II), (III), (IV), (V) and (VI) in which L and E are selected from the group consisting of Cyc and Phe and simultaneously one or more components selected from the compounds of the formulae (II), (III), (IV), (V) and (VI) in which one of the radicals L and E is selected from the group consisting of Cyc and Phe and the other radical is selected from the group consisting of -Phe-Phe-, -Phe-Cyc-, -Cyc-Cyc-, -G-Phe- and -G-Cyc-, and optionally one or more components selected from the compounds of the formulae (II), (III), (IV), (V) and (VI) in which the radicals L and E are selected from the group consisting of -Phe-Cyc-, -Cyc-Cyc-, -G-Phe- and -G-Cyc-.

In a smaller sub-group of the compounds of the formulae (II), (III), (IV), (V) and (VI), R' and R'' each, independently of one another, denote alkyl, alkenyl, alkoxy, alkoxyalkyl (oxaalkyl), alkenyloxy or alkanoyloxy having up to 8 C atoms. This smaller sub-group is called group A below, and the compounds are referred to by the sub-formulae (IIa), (IIIa), (IVa), (Va) and (VIa). In most of these compounds, R' and R'' are different from one another, one of these radicals usually being alkyl, alkenyl, alkoxy or alkoxy-alkyl (oxaalkyl).

In another smaller sub-group of the compounds of the formulae (II), (III), (IV), (V) and (VI), which is known as group B, E denotes

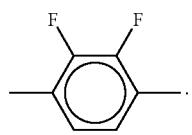

In the compounds of group B, which are referred to by the sub-formulae (IIb), (IIIb), (IVb), (Vb) and (VIb), R' and R'' are as defined for the compounds of the sub-formulae (IIa) to (VIa) and are preferably alkyl, alkenyl, alkoxy or alkoxyalkyl (oxaalkyl).

In a further smaller sub-group of the compounds of the formulae (II), (III), (IV), (V) and (VI), R'' denotes —CN. This sub-group is referred to below as group C, and the compounds of this sub-group are correspondingly described by sub-formulae (IIc), (IIIc), (IVc), (Vc) and (VIc). In the compounds of the sub-formulae (IIc), (IIIc), (IVc), (Vc) and (VIc), R' is as defined for the compounds of the sub-formulae (IIa) to (VIa) and is preferably alkyl, alkenyl, alkoxy or alkoxyalkyl (oxaalkyl).

Besides the preferred compounds of groups A, B and C, other compounds of the formulae (II), (III), (IV), (V) and (VI) having other variants of the proposed substituents are also customary. All these substances are obtainable by methods which are known from the literature or analogously thereto.

Besides the compounds of the general formula I according to the invention, the media according to the invention preferably comprise one or more compounds from groups A, B and/or C. The proportions by weight of the compounds from these groups in the media according to the invention are:

group A:

from 0 to 90%, preferably from 20 to 90%, in particular from 30 to 90%.

group B:

from 0 to 80%, preferably from 10 to 80%, in particular from 10 to 70%.

group C:

from 0 to 80%, preferably from 5 to 80%, in particular from 5 to 50%.

The media according to the invention preferably comprise from 1 to 40%, particularly preferably from 5 to 30%, of the compounds of the formula I according to the invention. Preference is furthermore given to media comprising more than 40%, in particular from 45 to 90%, of compounds of the formula I according to the invention. The media preferably comprise one, two, three, four or five compounds of the formula I according to the invention.

Examples of the compounds of the formulae (II), (III), (IV), (V) and (VI) are the compounds listed below:

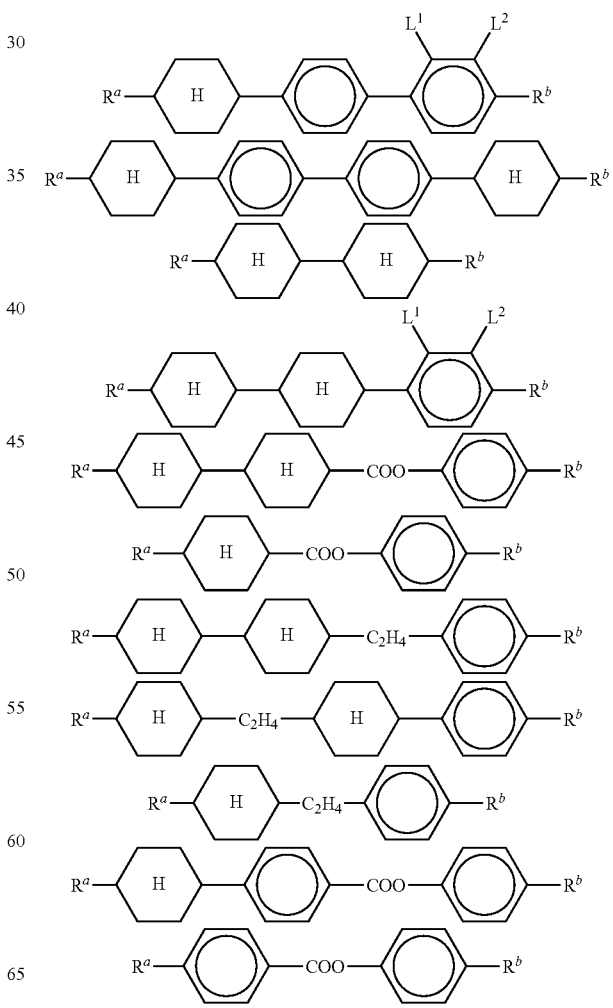

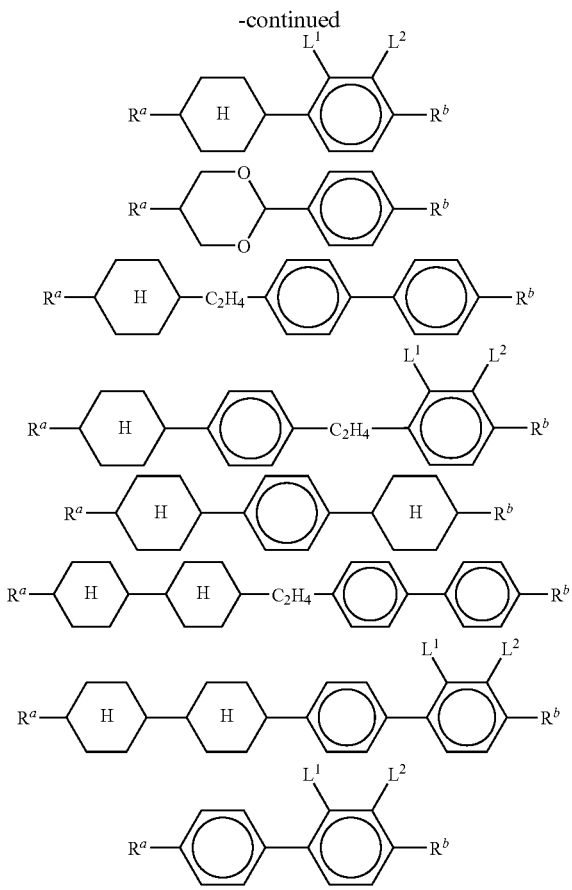

where $R^a$ and $R^b$, independently of one another, are —$C_pH_{2p+1}$ or —$OC_pH_{2p+1}$, and p=1, 2, 3, 4, 5, 6, 7 or 8, and $L^1$ and $L^2$, independently of one another, are —H or —F,

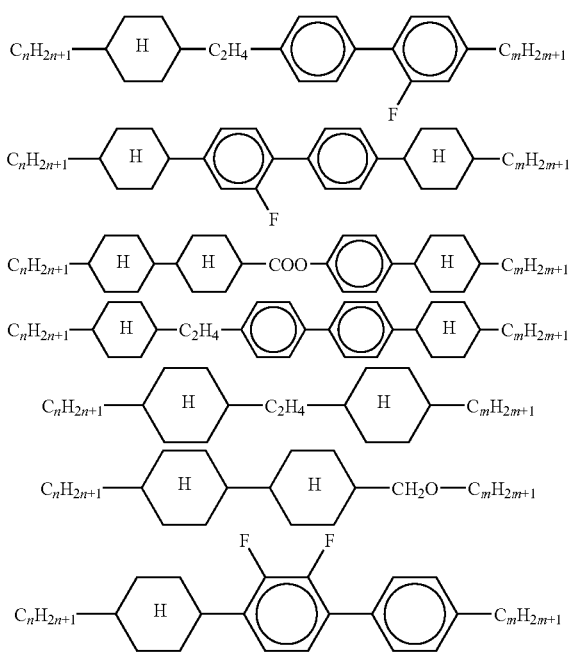

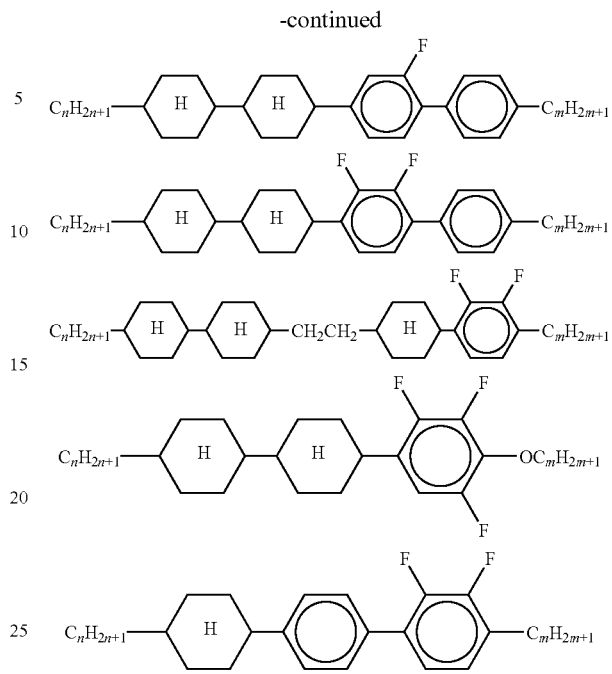

where m and n, independently of one another, are 1, 2, 3, 4, 5, 6, 7 or 8.

The media according to the invention are prepared in a manner conventional per se. In general, the components are dissolved in one another, preferably at elevated temperature. By means of suitable additives, the liquid-crystalline phases of the present invention can be modified in such a way that they can be used in all types of liquid-crystal display element that have been disclosed hitherto. Additives of this type are known to the person skilled in the art and are described in detail in the literature (H. Kelker/R. Hatz, Handbook of Liquid Crystals, Verlag Chemie, Weinheim, 1980). For example, pleochroic dyes can be used for the production of coloured guest-host systems or substances can be added in order to modify the dielectric anisotropy, the viscosity and/or the alignment of the nematic phases.

Owing to their negative Δε, the compounds of the formula I are particularly suitable for use in VA-TFT displays.

The present invention therefore also relates to electro-optical liquid-crystal display elements containing a liquid-crystalline medium according to the invention.

The invention is explained in greater detail below with reference to working examples, but without being restricted thereby.

Above and below, Δn denotes the optical anisotropy (589 nm, 20° C.) and Δε denotes the dielectric anisotropy (1 kHz, 20° C.).

The Δε and Δn values of the compounds according to the invention are obtained by extrapolation from liquid-crystalline mixtures consisting of 10% of the respective compound according to the invention and 90% of the commercially available liquid-crystal mixture ZLI-2857 (for Δε) or ZLI-4792 (for Δn) (Merck KGaA, Darmstadt). In cases of limited solubility, the compound is measured in a mixture comprising only 5% of the compound, which is noted by the addition (5%) after the values in question.

EXAMPLES

The starting substances can be obtained by generally accessible literature procedures or are commercially available. The reactions described are known from the literature.

Example 1

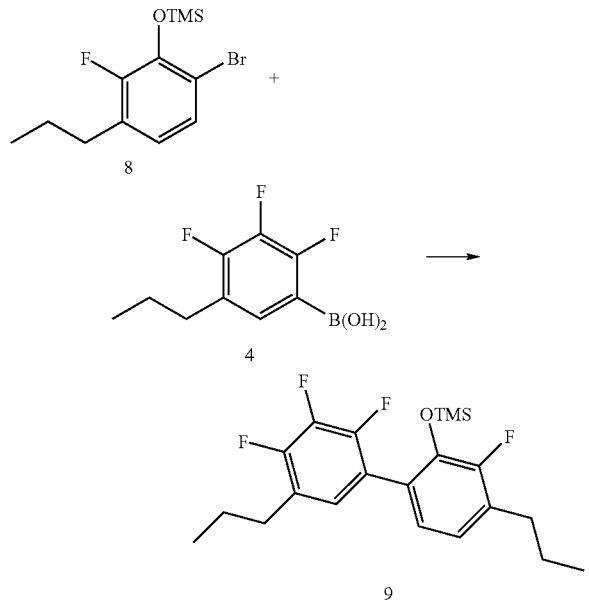

7.0 g (22.9 mmol) of the silyl ether 8 are dissolved in 20 ml of toluene under nitrogen, and 5.0 g (49.3 mmol) of sodium carbonate, 10 ml of water and 175 mg (0.2 mmol) of tetrakis(triphenylphosphine)palladium are added. A solution of 5.0 g (22.9 mmol) of the boronic acid 4 in 10 ml of absolute ethanol is slowly added to the reaction mixture at the boiling temperature. After refluxing for 5 hours and cooling, the phases are separated. The aqueous phase is extracted with MTB ether. The organic phase is dried over sodium sulfate and evaporated. The residue is chromatographed on silica gel, giving 6.5 g of the silyl ether 9 (yield: 71%).

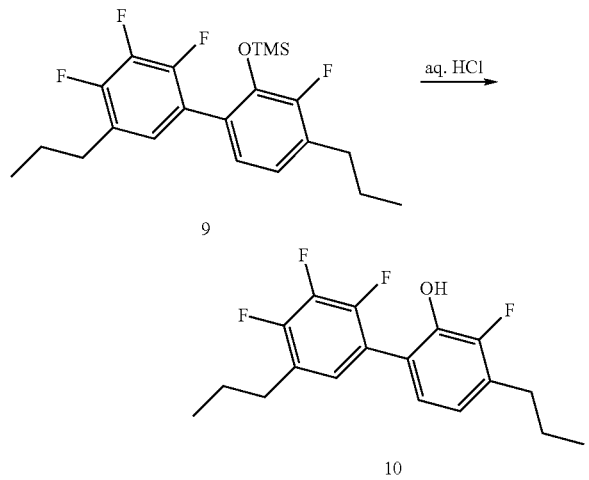

5.0 g (12.6 mmol) of the silyl ether 9 are dissolved in 40 ml of THF, and 10 ml of dil. HCl are added. The solution is stirred at room temperature until conversion is complete (TLC check). The solvent is subsequently removed, and the residue is taken up in 10 ml of dil. HCl solution and 20 ml of MTB ether. The aqueous phase is extracted three times with MTB ether. The organic phase is dried, evaporated and passed through silica gel, giving 3.7 g of the phenol 10 (yield: 90%).

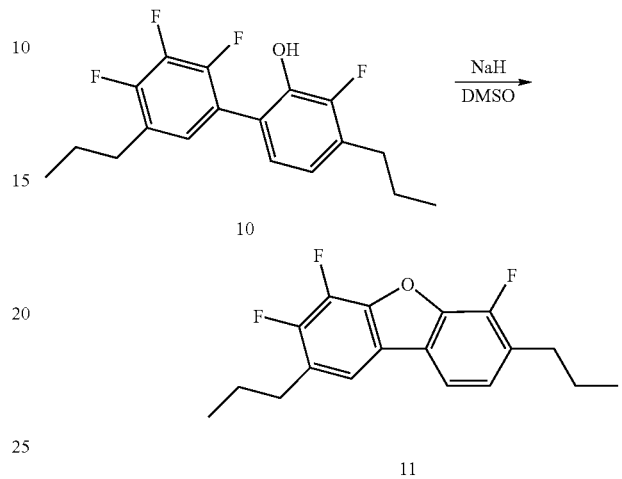

3.0 g (9.2 mmol) of the phenol 10 are dissolved in 40 ml of DMSO under nitrogen, 736 mg (18.4 mmol) of a 60% sodium hydride/mineral oil suspension are added, and the mixture is warmed to 120° C. After 5 hours at this temperature, the cooled batch is added to dilute HCl solution. The aqueous phase is extracted with MTB ether. The organic phase is dried over sodium sulfate, evaporated and chromatographed on silica gel, giving 1.8 g of the dibenzofuran 11 (yield: 62%).

Δε: −4.3
Δn: 0.064

The following compounds according to the invention are obtained analogously to Example 1 using the corresponding precursors:

Examples 2 to 64

| Example No. | $R^1$ | $R^2$ | Δε | Δn |
|---|---|---|---|---|
| 2 | H | H | | |
| 3 | H | $CH_3$ | | |
| 4 | H | $C_2H_5$ | | |
| 5 | H | $n-C_3H_7$ | | |
| 6 | H | $n-C_4H_9$ | | |
| 7 | H | $n-C_5H_{11}$ | | |
| 8 | H | $n-C_6H_{13}$ | | |
| 9 | H | $n-C_7H_{15}$ | | |
| 10 | $CH_3$ | H | | |
| 11 | $CH_3$ | $CH_3$ | | |
| 12 | $CH_3$ | $C_2H_5$ | | |
| 13 | $CH_3$ | $n-C_3H_7$ | | |
| 14 | $CH_3$ | $n-C_4H_9$ | | |
| 15 | $CH_3$ | $n-C_5H_{11}$ | | |

-continued

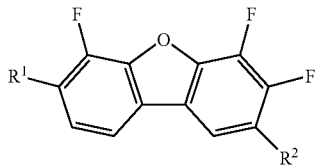

| Example No. | R¹ | R² | Δε | Δn |
|---|---|---|---|---|
| 16 | CH₃ | n-C₆H₁₃ | | |
| 17 | CH₃ | n-C₇H₁₅ | | |
| 18 | C₂H₅ | H | | |
| 19 | C₂H₅ | CH₃ | | |
| 20 | C₂H₅ | C₂H₅ | | |
| 21 | C₂H₅ | n-C₃H₇ | | |
| 22 | C₂H₅ | n-C₄H₉ | | |
| 23 | C₂H₅ | n-C₅H₁₁ | | |
| 24 | C₂H₅ | n-C₆H₁₃ | | |
| 25 | C₂H₅ | n-C₇H₁₅ | | |
| 26 | n-C₃H₇ | H | −2.8 | 0.110 |
| 27 | n-C₃H₇ | CH₃ | | |
| 28 | n-C₃H₇ | C₂H₅ | | |
| 29 | n-C₃H₇ | n-C₄H₉ | | |
| 30 | n-C₃H₇ | n-C₅H₁₁ | | |
| 31 | n-C₃H₇ | n-C₆H₁₃ | | |
| 32 | n-C₃H₇ | n-C₇H₁₅ | | |
| 33 | n-C₄H₉ | H | | |
| 34 | n-C₄H₉ | CH₃ | | |
| 35 | n-C₄H₉ | C₂H₅ | | |
| 36 | n-C₄H₉ | n-C₃H₇ | | |
| 37 | n-C₄H₉ | n-C₄H₉ | | |
| 38 | n-C₄H₉ | n-C₅H₁₁ | | |
| 39 | n-C₄H₉ | n-C₆H₁₃ | | |
| 40 | n-C₄H₉ | n-C₇H₁₅ | | |
| 41 | n-C₅H₁₁ | H | | |
| 42 | n-C₅H₁₁ | CH₃ | | |
| 43 | n-C₅H₁₁ | C₂H₅ | | |
| 44 | n-C₅H₁₁ | n-C₃H₇ | | |
| 45 | n-C₅H₁₁ | n-C₄H₉ | | |
| 46 | n-C₅H₁₁ | n-C₅H₁₁ | | |
| 47 | n-C₅H₁₁ | n-C₆H₁₃ | | |
| 48 | n-C₅H₁₁ | n-C₇H₁₅ | | |
| 49 | n-C₆H₁₃ | H | | |
| 50 | n-C₆H₁₃ | CH₃ | | |
| 51 | n-C₆H₁₃ | C₂H₅ | | |
| 52 | n-C₆H₁₃ | n-C₃H₇ | | |
| 53 | n-C₆H₁₃ | n-C₄H₉ | | |
| 54 | n-C₆H₁₃ | n-C₅H₁₁ | | |
| 55 | n-C₆H₁₃ | n-C₆H₁₃ | | |
| 56 | n-C₆H₁₃ | n-C₇H₁₅ | | |
| 57 | n-C₇H₁₅ | H | | |
| 58 | n-C₇H₁₅ | CH₃ | | |
| 59 | n-C₇H₁₅ | C₂H₅ | | |
| 60 | n-C₇H₁₅ | n-C₃H₇ | | |
| 61 | n-C₇H₁₅ | n-C₄H₉ | | |
| 62 | n-C₇H₁₅ | n-C₅H₁₁ | | |
| 63 | n-C₇H₁₅ | n-C₆H₁₃ | | |
| 64 | n-C₇H₁₅ | n-C₇H₁₅ | | |

Examples 65 to 128

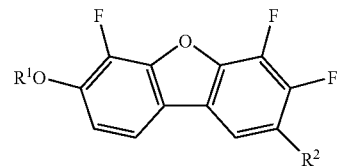

| Example No. | R¹ | R² | Δε | Δn |
|---|---|---|---|---|
| 65 | H | H | | |
| 66 | H | CH₃ | | |
| 67 | H | C₂H₅ | | |
| 68 | H | n-C₃H₇ | | |
| 69 | H | n-C₄H₉ | | |
| 70 | H | n-C₅H₁₁ | | |
| 71 | H | n-C₆H₁₃ | | |
| 72 | H | n-C₇H₁₅ | | |
| 73 | CH₃ | H | | |
| 74 | CH₃ | CH₃ | | |
| 75 | CH₃ | C₂H₅ | | |
| 76 | CH₃ | n-C₃H₇ | | |
| 77 | CH₃ | n-C₄H₉ | | |
| 78 | CH₃ | n-C₅H₁₁ | | |
| 79 | CH₃ | n-C₆H₁₃ | | |
| 80 | CH₃ | n-C₇H₁₅ | | |
| 81 | C₂H₅ | H | −7.8 | 0.149 (5%) |
| 82 | C₂H₅ | CH₃ | | |
| 83 | C₂H₅ | C₂H₅ | | |
| 84 | C₂H₅ | n-C₃H₇ | −9.1 | 0.107 (5%) |
| 85 | C₂H₅ | n-C₄H₉ | | |
| 86 | C₂H₅ | n-C₅H₁₁ | −8.4 | 0.088 |
| 87 | C₂H₅ | n-C₆H₁₃ | | |
| 88 | C₂H₅ | n-C₇H₁₅ | | |
| 89 | n-C₃H₇ | H | | |
| 90 | n-C₃H₇ | CH₃ | | |
| 91 | n-C₃H₇ | C₂H₅ | | |
| 92 | n-C₃H₇ | n-C₃H₇ | | |
| 93 | n-C₃H₇ | n-C₄H₉ | | |
| 94 | n-C₃H₇ | n-C₅H₁₁ | | |
| 95 | n-C₃H₇ | n-C₆H₁₃ | | |
| 96 | n-C₃H₇ | n-C₇H₁₅ | | |
| 97 | n-C₄H₉ | H | | |
| 98 | n-C₄H₉ | CH₃ | | |
| 99 | n-C₄H₉ | C₂H₅ | | |
| 100 | n-C₄H₉ | n-C₃H₇ | | |
| 101 | n-C₄H₉ | n-C₄H₉ | | |
| 102 | n-C₄H₉ | n-C₅H₁₁ | | |
| 103 | n-C₄H₉ | n-C₆H₁₃ | | |
| 104 | n-C₄H₉ | n-C₇H₁₅ | | |
| 105 | n-C₅H₁₁ | H | | |
| 106 | n-C₅H₁₁ | CH₃ | | |
| 107 | n-C₅H₁₁ | C₂H₅ | | |
| 108 | n-C₅H₁₁ | n-C₃H₇ | | |
| 109 | n-C₅H₁₁ | n-C₄H₉ | | |
| 110 | n-C₅H₁₁ | n-C₅H₁₁ | | |
| 111 | n-C₅H₁₁ | n-C₆H₁₃ | | |
| 112 | n-C₅H₁₁ | n-C₇H₁₅ | | |
| 113 | n-C₆H₁₃ | H | | |
| 114 | n-C₆H₁₃ | CH₃ | | |
| 115 | n-C₆H₁₃ | C₂H₅ | | |
| 116 | n-C₆H₁₃ | n-C₃H₇ | | |
| 117 | n-C₆H₁₃ | n-C₄H₉ | | |
| 118 | n-C₆H₁₃ | n-C₅H₁₁ | | |
| 119 | n-C₆H₁₃ | n-C₆H₁₃ | | |
| 120 | n-C₆H₁₃ | n-C₇H₁₅ | | |
| 121 | n-C₇H₁₅ | H | | |
| 122 | n-C₇H₁₅ | CH₃ | | |
| 123 | n-C₇H₁₅ | C₂H₅ | | |
| 124 | n-C₇H₁₅ | n-C₃H₇ | | |
| 125 | n-C₇H₁₅ | n-C₄H₉ | | |
| 126 | n-C₇H₁₅ | n-C₅H₁₁ | | |
| 127 | n-C₇H₁₅ | n-C₆H₁₃ | | |
| 128 | n-C₇H₁₅ | n-C₇H₁₅ | | |

Examples 129 to 192

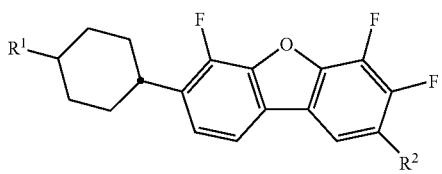

Examples 193 to 256

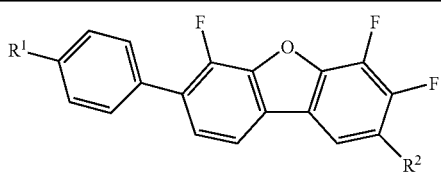

| Example No. | R¹ | R² |
|---|---|---|
| 129, 193 | H | H |
| 130, 194 | H | CH₃ |
| 131, 195 | H | C₂H₅ |
| 132, 196 | H | n-C₃H₇ |
| 133, 197 | H | n-C₄H₉ |
| 134, 198 | H | n-C₅H₁₁ |
| 135, 199 | H | n-C₆H₁₃ |
| 136, 200 | H | n-C₇H₁₅ |
| 137, 201 | CH₃ | H |
| 138, 202 | CH₃ | CH₃ |
| 139, 203 | CH₃ | C₂H₅ |
| 140, 204 | CH₃ | n-C₃H₇ |
| 141, 205 | CH₃ | n-C₄H₉ |
| 142, 206 | CH₃ | n-C₅H₁₁ |
| 143, 207 | CH₃ | n-C₆H₁₃ |
| 144, 208 | CH₃ | n-C₇H₁₅ |
| 145, 209 | C₂H₅ | H |
| 146, 210 | C₂H₅ | CH₃ |
| 147, 211 | C₂H₅ | C₂H₅ |
| 148, 212 | C₂H₅ | n-C₃H₇ |
| 149, 213 | C₂H₅ | n-C₄H₉ |
| 150, 214 | C₂H₅ | n-C₅H₁₁ |
| 151, 215 | C₂H₅ | n-C₆H₁₃ |
| 152, 216 | C₂H₅ | n-C₇H₁₅ |
| 153, 217 | n-C₃H₇ | H |
| 154, 218 | n-C₃H₇ | CH₃ |
| 155, 219 | n-C₃H₇ | C₂H₅ |
| 156, 220 | n-C₃H₇ | n-C₃H₇ |
| 157, 221 | n-C₃H₇ | n-C₄H₉ |
| 158, 222 | n-C₃H₇ | n-C₅H₁₁ |
| 159, 223 | n-C₃H₇ | n-C₆H₁₃ |
| 160, 224 | n-C₃H₇ | n-C₇H₁₅ |
| 161, 225 | n-C₄H₉ | H |
| 162, 226 | n-C₄H₉ | CH₃ |
| 163, 227 | n-C₄H₉ | C₂H₅ |
| 164, 228 | n-C₄H₉ | n-C₃H₇ |
| 165, 229 | n-C₄H₉ | n-C₄H₉ |
| 166, 230 | n-C₄H₉ | n-C₅H₁₁ |
| 167, 231 | n-C₄H₉ | n-C₆H₁₃ |
| 168, 232 | n-C₄H₉ | n-C₇H₁₅ |
| 169, 233 | n-C₅H₁₁ | H |
| 170, 234 | n-C₅H₁₁ | CH₃ |
| 171, 235 | n-C₅H₁₁ | C₂H₅ |
| 172, 236 | n-C₅H₁₁ | n-C₃H₇ |
| 173, 237 | n-C₅H₁₁ | n-C₄H₉ |
| 174, 238 | n-C₅H₁₁ | n-C₅H₁₁ |
| 175, 239 | n-C₅H₁₁ | n-C₆H₁₃ |
| 176, 240 | n-C₅H₁₁ | n-C₇H₁₅ |
| 177, 241 | n-C₆H₁₃ | H |
| 178, 242 | n-C₆H₁₃ | CH₃ |

-continued

| Example No. | R¹ | R² |
|---|---|---|
| 179, 243 | n-C₆H₁₃ | C₂H₅ |
| 180, 244 | n-C₆H₁₃ | n-C₃H₇ |
| 181, 245 | n-C₆H₁₃ | n-C₄H₉ |
| 182, 246 | n-C₆H₁₃ | n-C₅H₁₁ |
| 183, 247 | n-C₆H₁₃ | n-C₆H₁₃ |
| 184, 248 | n-C₆H₁₃ | n-C₇H₁₅ |
| 185, 249 | n-C₇H₁₅ | H |
| 186, 250 | n-C₇H₁₅ | CH₃ |
| 187, 251 | n-C₇H₁₅ | C₂H₅ |
| 188, 252 | n-C₇H₁₅ | n-C₃H₇ |
| 189, 253 | n-C₇H₁₅ | n-C₄H₉ |
| 190, 254 | n-C₇H₁₅ | n-C₅H₁₁ |
| 191, 255 | n-C₇H₁₅ | n-C₆H₁₃ |
| 192, 256 | n-C₇H₁₅ | n-C₇H₁₅ |

Examples 257 to 320

Examples 321 to 384

| Example No. | R¹ | R² |
|---|---|---|
| 257, 321 | H | H |
| 258, 322 | H | CH₃ |
| 259, 323 | H | C₂H₅ |
| 260, 324 | H | n-C₃H₇ |
| 261, 325 | H | n-C₄H₉ |
| 262, 326 | H | n-C₅H₁₁ |
| 263, 327 | H | n-C₆H₁₃ |
| 264, 328 | H | n-C₇H₁₅ |
| 265, 329 | CH₃ | H |
| 266, 330 | CH₃ | CH₃ |

-continued

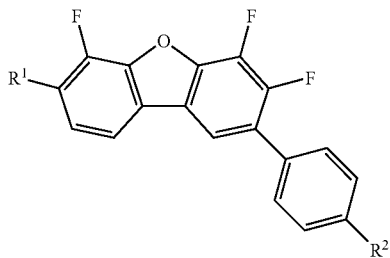

| Example No. | R¹ | R² |
|---|---|---|
| 267, 331 | $CH_3$ | $C_2H_5$ |
| 268, 332 | $CH_3$ | $n-C_3H_7$ |
| 269, 333 | $CH_3$ | $n-C_4H_9$ |
| 270, 334 | $CH_3$ | $n-C_5H_{11}$ |
| 271, 335 | $CH_3$ | $n-C_6H_{13}$ |
| 272, 336 | $CH_3$ | $n-C_7H_{15}$ |
| 273, 337 | $C_2H_5$ | H |
| 274, 338 | $C_2H_5$ | $CH_3$ |
| 275, 339 | $C_2H_5$ | $C_2H_5$ |
| 276, 340 | $C_2H_5$ | $n-C_3H_7$ |
| 277, 341 | $C_2H_5$ | $n-C_4H_9$ |
| 278, 342 | $C_2H_5$ | $n-C_5H_{11}$ |
| 279, 343 | $C_2H_5$ | $n-C_6H_{13}$ |
| 280, 344 | $C_2H_5$ | $n-C_7H_{15}$ |
| 281, 345 | $n-C_3H_7$ | H |
| 282, 346 | $n-C_3H_7$ | $CH_3$ |
| 283, 347 | $n-C_3H_7$ | $C_2H_5$ |
| 284, 348 | $n-C_3H_7$ | $n-C_3H_7$ |
| 285, 349 | $n-C_3H_7$ | $n-C_4H_9$ |
| 286, 350 | $n-C_3H_7$ | $n-C_5H_{11}$ |
| 287, 351 | $n-C_3H_7$ | $n-C_6H_{13}$ |
| 288, 352 | $n-C_3H_7$ | $n-C_7H_{15}$ |
| 289, 353 | $n-C_4H_9$ | H |
| 290, 354 | $n-C_4H_9$ | $CH_3$ |
| 291, 355 | $n-C_4H_9$ | $C_2H_5$ |
| 292, 356 | $n-C_4H_9$ | $n-C_3H_7$ |
| 293, 357 | $n-C_4H_9$ | $n-C_4H_9$ |
| 294, 358 | $n-C_4H_9$ | $n-C_5H_{11}$ |
| 295, 359 | $n-C_4H_9$ | $n-C_6H_{13}$ |
| 296, 360 | $n-C_4H_9$ | $n-C_7H_{15}$ |
| 297, 361 | $n-C_5H_{11}$ | H |
| 298, 362 | $n-C_5H_{11}$ | $CH_3$ |
| 299, 363 | $n-C_5H_{11}$ | $C_2H_5$ |
| 300, 364 | $n-C_5H_{11}$ | $n-C_3H_7$ |
| 301, 365 | $n-C_5H_{11}$ | $n-C_4H_9$ |
| 302, 366 | $n-C_5H_{11}$ | $n-C_5H_{11}$ |
| 303, 367 | $n-C_5H_{11}$ | $n-C_6H_{13}$ |
| 304, 368 | $n-C_5H_{11}$ | $n-C_7H_{15}$ |
| 305, 369 | $n-C_6H_{13}$ | H |
| 306, 370 | $n-C_6H_{13}$ | $CH_3$ |
| 307, 371 | $n-C_6H_{13}$ | $C_2H_5$ |
| 308, 372 | $n-C_6H_{13}$ | $n-C_3H_7$ |
| 309, 373 | $n-C_6H_{13}$ | $n-C_4H_9$ |
| 310, 374 | $n-C_6H_{13}$ | $n-C_5H_{11}$ |
| 311, 375 | $n-C_6H_{13}$ | $n-C_6H_{13}$ |
| 312, 376 | $n-C_6H_{13}$ | $n-C_7H_{15}$ |
| 313, 377 | $n-C_7H_{15}$ | H |
| 314, 378 | $n-C_7H_{15}$ | $CH_3$ |
| 315, 379 | $n-C_7H_{15}$ | $C_2H_5$ |
| 316, 380 | $n-C_7H_{15}$ | $n-C_3H_7$ |
| 317, 381 | $n-C_7H_{15}$ | $n-C_4H_9$ |
| 318, 382 | $n-C_7H_{15}$ | $n-C_5H_{11}$ |
| 319, 383 | $n-C_7H_{15}$ | $n-C_6H_{13}$ |
| 320, 384 | $n-C_7H_{15}$ | $n-C_7H_{15}$ |

Examples 385 to 448

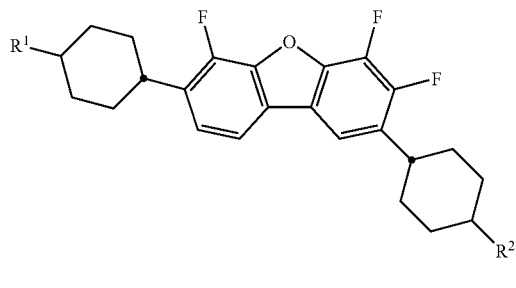

Examples 449 to 512

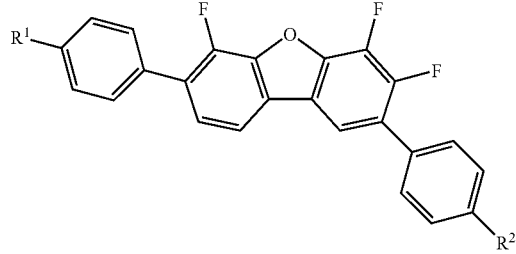

| Example No. | R¹ | R² |
|---|---|---|
| 385, 449 | H | H |
| 386, 450 | H | $CH_3$ |
| 387, 451 | H | $C_2H_5$ |
| 388, 452 | H | $n-C_3H_7$ |
| 389, 453 | H | $n-C_4H_9$ |
| 390, 454 | H | $n-C_5H_{11}$ |
| 391, 455 | H | $n-C_6H_{13}$ |
| 392, 456 | H | $n-C_7H_{15}$ |
| 393, 457 | $CH_3$ | H |
| 394, 458 | $CH_3$ | $CH_3$ |
| 395, 459 | $CH_3$ | $C_2H_5$ |
| 396, 460 | $CH_3$ | $n-C_3H_7$ |
| 397, 461 | $CH_3$ | $n-C_4H_9$ |
| 398, 462 | $CH_3$ | $n-C_5H_{11}$ |
| 399, 463 | $CH_3$ | $n-C_6H_{13}$ |
| 400, 464 | $CH_3$ | $n-C_7H_{15}$ |
| 401, 465 | $C_2H_5$ | H |
| 402, 466 | $C_2H_5$ | $CH_3$ |
| 403, 467 | $C_2H_5$ | $C_2H_5$ |
| 404, 468 | $C_2H_5$ | $n-C_3H_7$ |
| 405, 469 | $C_2H_5$ | $n-C_4H_9$ |
| 406, 470 | $C_2H_5$ | $n-C_5H_{11}$ |
| 407, 471 | $C_2H_5$ | $n-C_6H_{13}$ |
| 408, 472 | $C_2H_5$ | $n-C_7H_{15}$ |
| 409, 473 | $n-C_3H_7$ | H |
| 410, 474 | $n-C_3H_7$ | $CH_3$ |
| 411, 475 | $n-C_3H_7$ | $C_2H_5$ |
| 412, 476 | $n-C_3H_7$ | $n-C_3H_7$ |
| 413, 477 | $n-C_3H_7$ | $n-C_4H_9$ |
| 414, 478 | $n-C_3H_7$ | $n-C_5H_{11}$ |
| 415, 479 | $n-C_3H_7$ | $n-C_6H_{13}$ |
| 416, 480 | $n-C_3H_7$ | $n-C_7H_{15}$ |
| 417, 481 | $n-C_4H_9$ | H |
| 418, 482 | $n-C_4H_9$ | $CH_3$ |
| 419, 483 | $n-C_4H_9$ | $C_2H_5$ |
| 420, 484 | $n-C_4H_9$ | $n-C_3H_7$ |
| 421, 485 | $n-C_4H_9$ | $n-C_4H_9$ |
| 422, 486 | $n-C_4H_9$ | $n-C_5H_{11}$ |
| 423, 487 | $n-C_4H_9$ | $n-C_6H_{13}$ |
| 424, 488 | $n-C_4H_9$ | $n-C_7H_{15}$ |
| 425, 489 | $n-C_5H_{11}$ | H |
| 426, 490 | $n-C_5H_{11}$ | $CH_3$ |
| 427, 491 | $n-C_5H_{11}$ | $C_2H_5$ |
| 428, 492 | $n-C_5H_{11}$ | $n-C_3H_7$ |
| 429, 493 | $n-C_5H_{11}$ | $n-C_4H_9$ |

-continued

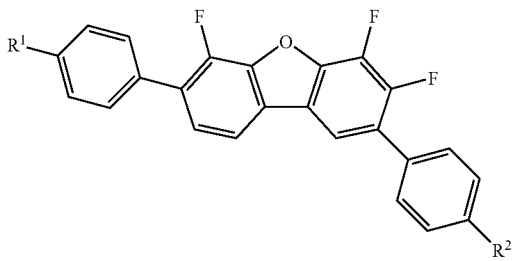

| Example No. | R¹ | R² |
|---|---|---|
| 430, 494 | n-C$_5$H$_{11}$ | n-C$_5$H$_{11}$ |
| 431, 495 | n-C$_5$H$_{11}$ | n-C$_6$H$_{13}$ |
| 432, 496 | n-C$_5$H$_{11}$ | n-C$_7$H$_{15}$ |
| 433, 497 | n-C$_6$H$_{13}$ | H |
| 434, 498 | n-C$_6$H$_{13}$ | CH$_3$ |
| 435, 499 | n-C$_6$H$_{13}$ | C$_2$H$_5$ |
| 436, 500 | n-C$_6$H$_{13}$ | n-C$_3$H$_7$ |
| 437, 501 | n-C$_6$H$_{13}$ | n-C$_4$H$_9$ |
| 438, 502 | n-C$_6$H$_{13}$ | n-C$_5$H$_{11}$ |
| 439, 503 | n-C$_6$H$_{13}$ | n-C$_6$H$_{13}$ |
| 440, 504 | n-C$_6$H$_{13}$ | n-C$_7$H$_{15}$ |
| 441, 505 | n-C$_7$H$_{15}$ | H |
| 442, 506 | n-C$_7$H$_{15}$ | CH$_3$ |
| 443, 507 | n-C$_7$H$_{15}$ | C$_2$H$_5$ |
| 444, 508 | n-C$_7$H$_{15}$ | n-C$_3$H$_7$ |
| 445, 509 | n-C$_7$H$_{15}$ | n-C$_4$H$_9$ |
| 446, 510 | n-C$_7$H$_{15}$ | n-C$_5$H$_{11}$ |
| 447, 511 | n-C$_7$H$_{15}$ | n-C$_6$H$_{13}$ |
| 448, 512 | n-C$_7$H$_{15}$ | n-C$_7$H$_{15}$ |

Examples 513 to 576

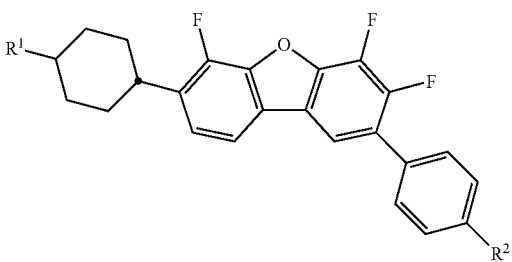

Examples 577 to 640

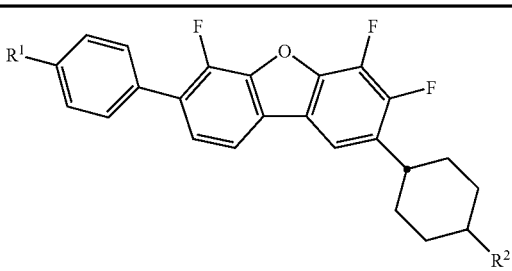

| Example No. | R¹ | R² |
|---|---|---|
| 513, 577 | H | H |
| 514, 578 | H | CH$_3$ |
| 515, 579 | H | C$_2$H$_5$ |

-continued

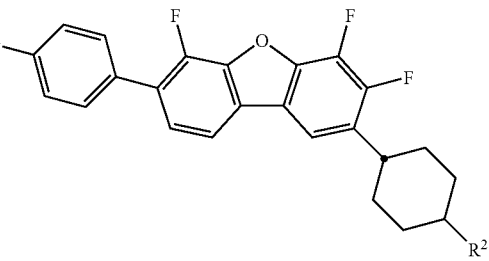

| Example No. | R¹ | R² |
|---|---|---|
| 516, 580 | H | n-C$_3$H$_7$ |
| 517, 581 | H | n-C$_4$H$_9$ |
| 518, 582 | H | n-C$_5$H$_{11}$ |
| 519, 583 | H | n-C$_6$H$_{13}$ |
| 520, 584 | H | n-C$_7$H$_{15}$ |
| 521, 585 | CH$_3$ | H |
| 522, 586 | CH$_3$ | CH$_3$ |
| 523, 587 | CH$_3$ | C$_2$H$_5$ |
| 524, 588 | CH$_3$ | n-C$_3$H$_7$ |
| 525, 589 | CH$_3$ | n-C$_4$H$_9$ |
| 526, 590 | CH$_3$ | n-C$_5$H$_{11}$ |
| 527, 591 | CH$_3$ | n-C$_6$H$_{13}$ |
| 528, 592 | CH$_3$ | n-C$_7$H$_{15}$ |
| 529, 593 | C$_2$H$_5$ | H |
| 530, 594 | C$_2$H$_5$ | CH$_3$ |
| 531, 595 | C$_2$H$_5$ | C$_2$H$_5$ |
| 532, 596 | C$_2$H$_5$ | n-C$_3$H$_7$ |
| 533, 597 | C$_2$H$_5$ | n-C$_4$H$_9$ |
| 534, 598 | C$_2$H$_5$ | n-C$_5$H$_{11}$ |
| 535, 599 | C$_2$H$_5$ | n-C$_6$H$_{13}$ |
| 536, 600 | C$_2$H$_5$ | n-C$_7$H$_{15}$ |
| 537, 601 | n-C$_3$H$_7$ | H |
| 538, 602 | n-C$_3$H$_7$ | CH$_3$ |
| 539, 603 | n-C$_3$H$_7$ | C$_2$H$_5$ |
| 540, 604 | n-C$_3$H$_7$ | n-C$_3$H$_7$ |
| 541, 605 | n-C$_3$H$_7$ | n-C$_4$H$_9$ |
| 542, 606 | n-C$_3$H$_7$ | n-C$_5$H$_{11}$ |
| 543, 607 | n-C$_3$H$_7$ | n-C$_6$H$_{13}$ |
| 544, 608 | n-C$_3$H$_7$ | n-C$_7$H$_{15}$ |
| 545, 609 | n-C$_4$H$_9$ | H |
| 546, 610 | n-C$_4$H$_9$ | CH$_3$ |
| 547, 611 | n-C$_4$H$_9$ | C$_2$H$_5$ |
| 548, 612 | n-C$_4$H$_9$ | n-C$_3$H$_7$ |
| 549, 613 | n-C$_4$H$_9$ | n-C$_4$H$_9$ |
| 550, 614 | n-C$_4$H$_9$ | n-C$_5$H$_{11}$ |
| 551, 615 | n-C$_4$H$_9$ | n-C$_6$H$_{13}$ |
| 552, 616 | n-C$_4$H$_9$ | n-C$_7$H$_{15}$ |
| 553, 617 | n-C$_5$H$_{11}$ | H |
| 554, 618 | n-C$_5$H$_{11}$ | CH$_3$ |
| 555, 619 | n-C$_5$H$_{11}$ | C$_2$H$_5$ |
| 556, 620 | n-C$_5$H$_{11}$ | n-C$_3$H$_7$ |
| 557, 621 | n-C$_5$H$_{11}$ | n-C$_4$H$_9$ |
| 558, 622 | n-C$_5$H$_{11}$ | n-C$_5$H$_{11}$ |
| 559, 623 | n-C$_5$H$_{11}$ | n-C$_6$H$_{13}$ |
| 560, 624 | n-C$_5$H$_{11}$ | n-C$_7$H$_{15}$ |
| 561, 625 | n-C$_6$H$_{13}$ | H |
| 562, 626 | n-C$_6$H$_{13}$ | CH$_3$ |
| 563, 627 | n-C$_6$H$_{13}$ | C$_2$H$_5$ |
| 564, 628 | n-C$_6$H$_{13}$ | n-C$_3$H$_7$ |
| 565, 629 | n-C$_6$H$_{13}$ | n-C$_4$H$_9$ |
| 566, 630 | n-C$_6$H$_{13}$ | n-C$_5$H$_{11}$ |
| 567, 631 | n-C$_6$H$_{13}$ | n-C$_6$H$_{13}$ |
| 568, 632 | n-C$_6$H$_{13}$ | n-C$_7$H$_{15}$ |
| 569, 633 | n-C$_7$H$_{15}$ | H |
| 570, 634 | n-C$_7$H$_{15}$ | CH$_3$ |
| 571, 635 | n-C$_7$H$_{15}$ | C$_2$H$_5$ |
| 572, 636 | n-C$_7$H$_{15}$ | n-C$_3$H$_7$ |
| 573, 637 | n-C$_7$H$_{15}$ | n-C$_4$H$_9$ |
| 574, 638 | n-C$_7$H$_{15}$ | n-C$_5$H$_{11}$ |
| 575, 639 | n-C$_7$H$_{15}$ | n-C$_6$H$_{13}$ |
| 576, 640 | n-C$_7$H$_{15}$ | n-C$_7$H$_{15}$ |

Example 641

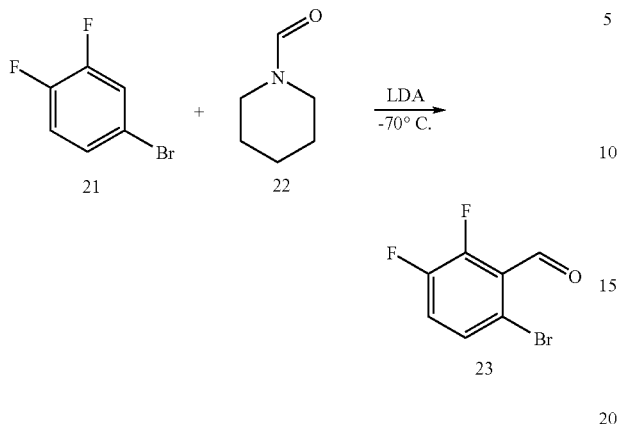

220 ml (440 mmol) of a 2M solution of lithium diisopropylamide in cyclohexane/ethylbenzene/THF are added under nitrogen and at −70° C. to a solution of 77.2 g (400 mmol) of the aromatic compound 21 in 500 ml of THF. After 1.5 hours at the low temperature, 55.5 ml (500 mmol) of N-formylpiperidine 22 are added to the batch at −50° C. to −40° C. After 3 hours at −40° C., the batch is hydrolysed at 0° C. and acidified using hydrochloric acid. The aqueous phase is extracted with MTB ether, and the organic phase is washed with sat. sodium chloride solution, dried over sodium sulfate, evaporated and passed through silica gel (MTB ether/n-heptane 1:20), giving 72.1 g (81%) of the aldehyde 23.

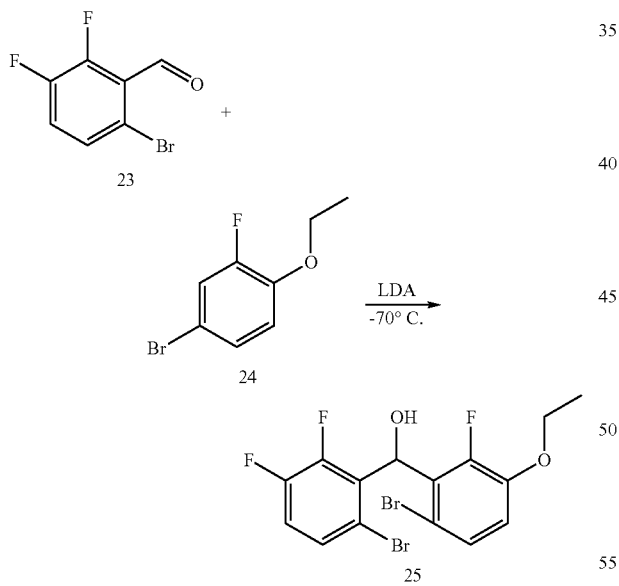

16.1 ml (120 mmol) of a 2M solution of lithium diisopropylamide in cyclo-hexane/ethylbenzene/THF are added under nitrogen and at −70° C. to a solution of 24.0 g (110 mmol) of the aromatic compound 24 in 150 ml of THF. After 1.5 hours at the low temperature, 22.1 g (100 mmol) of the aldehyde 23, dissolved in 50 ml of THF, are added to the batch. After 3 hours at −70° C., the batch is warmed to room temperature, hydrolysed and acidified using hydrochloric acid. The aqueous phase is extracted with MTB ether, and the organic phase is washed with sat. sodium chloride solution, dried over sodium sulfate, evaporated and passed through silica gel (MTB ether/n-heptane 1:10), giving 40.2 g (83%) of the diphenyl-methanol 25.

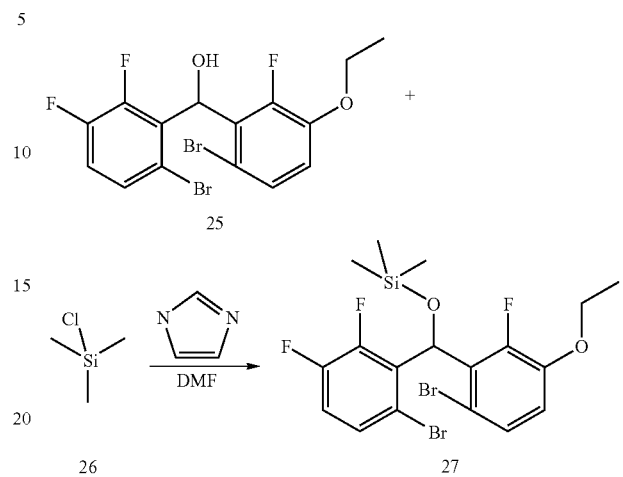

Under nitrogen, 14.7 g (213 mmol) of imidazole and 35.0 g (79.5 mmol) of the diphenylmethanol 25 are dissolved in 100 ml of DMF, 14.4 ml of trimethylsilyl chloride 26 are added, and the mixture is stirred overnight at room temperature. Sat. sodium chloride solution is added to the batch, which is extracted with MTB ether. The organic phase is dried over sodium sulfate, evaporated and passed through silica gel (MTB ether/n-heptane 1:20), giving 37.9 g (93%) of the silyl ether 27.

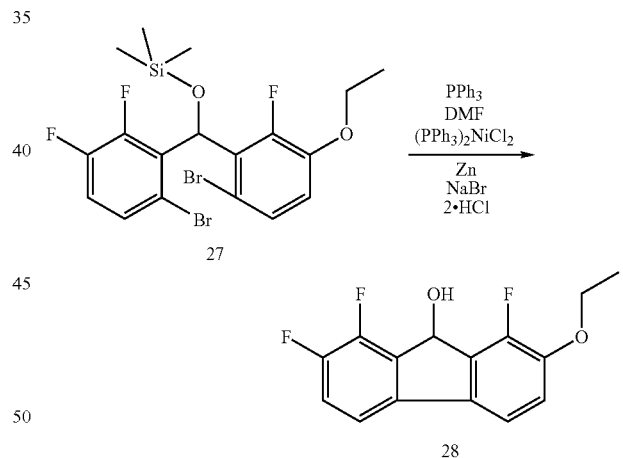

200 ml of DMF are added under nitrogen to 12.4 g (189 mmol) of zinc, 19.6 g (30 mmol) of bistriphenylphosphinenickel(II) chloride, 18.5 g (180 mmol) of sodium bromide and 47.6 g (180 mmol) of triphenylphosphine, and the mixture is warmed to 80° C. After 30 minutes, 30.7 g (60 mmol) of the silyl ether 27, dissolved in 50 ml of DMF, are added dropwise to the batch. After 3 days, water is added to the cooled batch, which is extracted with MTB ether. The organic phase is washed with sat. sodium chloride solution, dried over sodium sulfate and evaporated. The residue is taken up in THF, and conc. hydrochloric acid is added. After complete conversion (TLC), sat. sodium chloride solution is added to the batch, which is extracted with MTB ether. The organic phase is washed with sat. sodium chloride solution, dried over sodium sulfate and evaporated. Chromatography (MTB ether/n-heptane 1:1) on silica gel gives 2.5 g (15%) of the fluorenol 28.

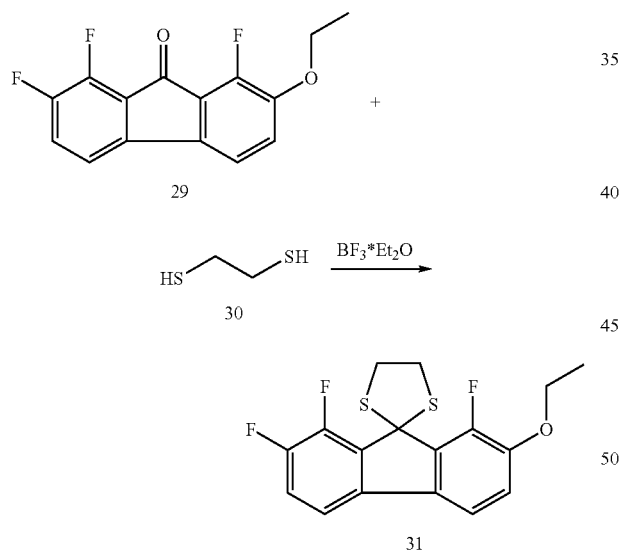

15 g of pyridinium chlorochromate (PCC) are added under nitrogen to a suspension of 40 g of Celite in 150 ml of dichloromethane. A solution of 10.0 g (35.6 mmol) of the fluorenol 28 in 25 ml of dichloromethane is subsequently added to the suspension. The batch is stirred overnight at room temperature. The Celite is separated off and washed with dichloro-methane. The organic phase is evaporated and passed through silica gel (MTB ether/n-heptane 1:3), giving 9.0 g (91%) of the fluorenone 29.

16.1 ml of boron trifluoride/diethyl ether complex are added under nitrogen and at −10° C. to a solution of 8.5 g (30.6 mmol) of the fluorenone 29 and 3.8 ml (45 mmol) of ethanedithiol 30 in 50 ml of dichloromethane. The batch thaws overnight and is carefully added to sat. sodium hydrogen-carbonate solution. The pH is adjusted to 8. The aqueous phase is extracted with dichloromethane, and the organic phase is washed with sat. sodium chloride solution, dried over sodium sulfate and evaporated. The residue is passed through silica gel (MTB ether/n-heptane 1:15), giving 9.6 g (89%) of the thioketal 31.

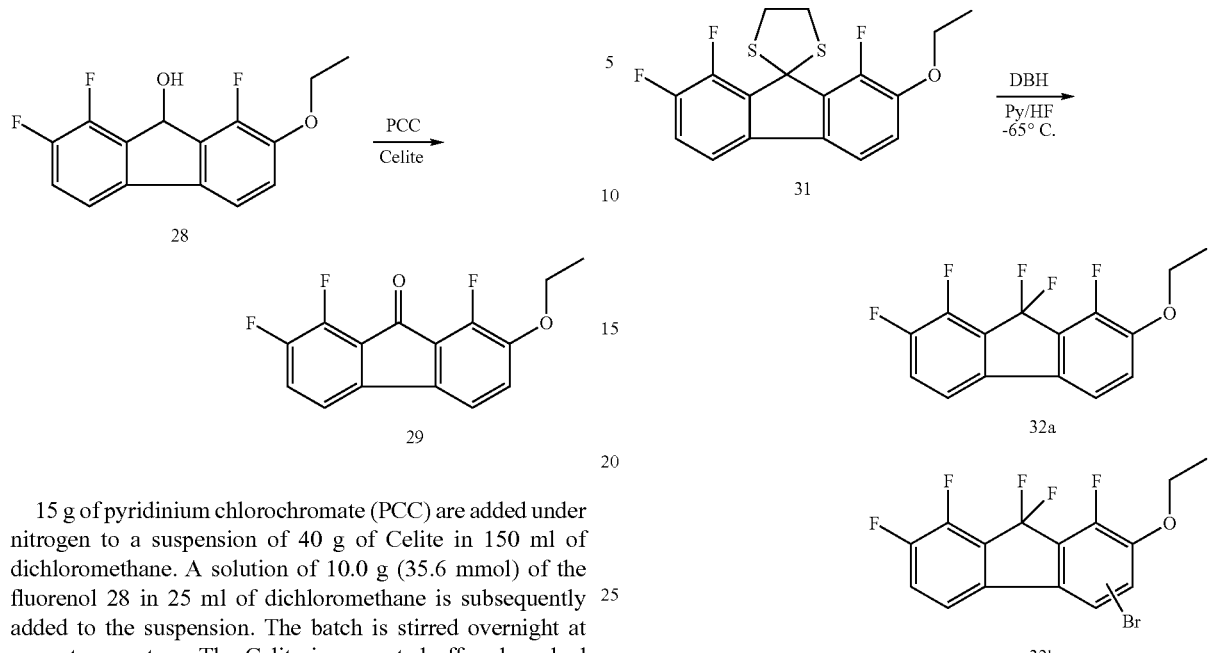

A solution of 9.0 g (25.4 mmol) of the thioketal 31 in 50 ml of dichloromethane is added under nitrogen and at a temperature of below −65° C. to a suspension of 28.6 g (100 mmol) of 1,3-dibromo-5,5-dimethylhydantoin in 150 ml of dichloromethane and 29.2 ml of a 65% solution of HF in pyridine. After 5 hours, the cooling is removed, and the batch is stirred overnight.

The batch is subsequently added to 1 l of ice-cooled 1N sodium hydroxide solution to which 35 ml of 19% sodium hydrogensulfite solution have been added. The pH is adjusted to 8. The aqueous phase is extracted with dichloromethane, and the organic phase is washed with sat. sodium chloride solution, dried over sodium sulfate, evaporated and passed through silica gel (MTB ether/n-heptane 1:30), giving 8 g of a mixture of the fluorenes 32a and 32b.

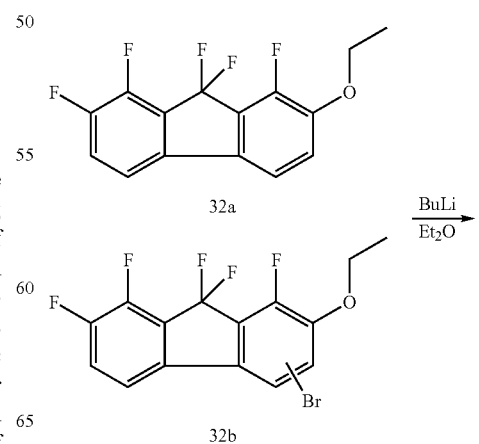

-continued

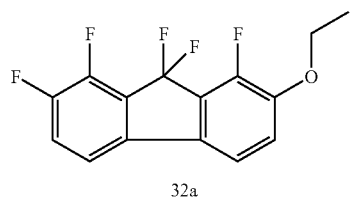
32a 8 g of the fluorene mixture are dissolved in 50 ml of diethyl ether under nitrogen, and 15.7 ml (25.0 mmol) of a 15% solution of butyllithium in n-hexane are added at −70° C. After 1 hour, 10 ml of a 1:1 THF/water mixture are added to the solution, and the batch is warmed to room temperature. The batch is washed with sat. sodium chloride solution, dried over sodium sulfate and evaporated. The residue obtained is passed through silica gel (MTB ether/n-heptane 1:30), giving 5.3 g (70%, based on the preceding step) of the fluorene 32a.

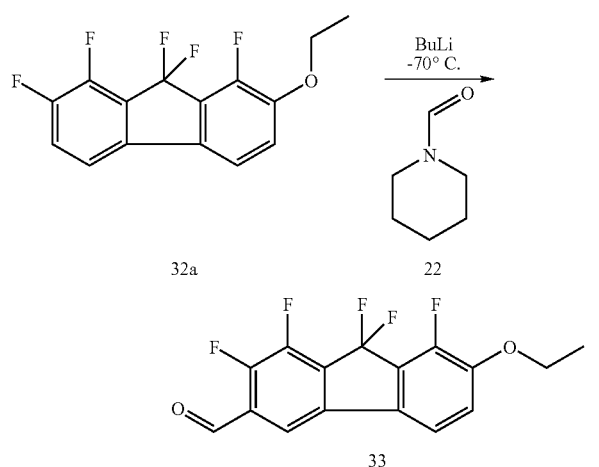

10.7 ml (17.0 mmol) of a 15% solution of butyllithium in n-hexane are added under nitrogen and at −70° C. to a solution of 5.0 g (16.7 mmol) of the fluorene 32a in 75 ml of THF. After 1.5 hours at the low temperature, 2.2 ml (20 mmol) of N-formylpiperidine 22 are added to the batch at −50° C. to −40° C. After 3 hours at −40° C., the batch is hydrolysed at 0° C. and acidified using hydrochloric acid. The aqueous phase is extracted with MTB ether, and the organic phase is washed with sat. sodium chloride solution, dried over sodium sulfate, evaporated and passed through silica gel (MTB ether/n-heptane 1:15), giving 4.3 g (79%) of the aldehyde 33.

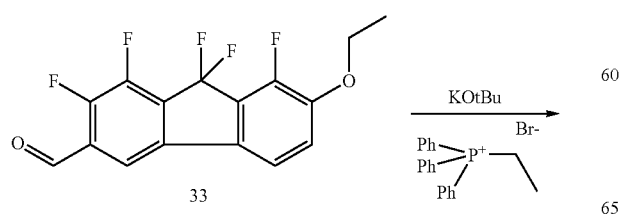

-continued

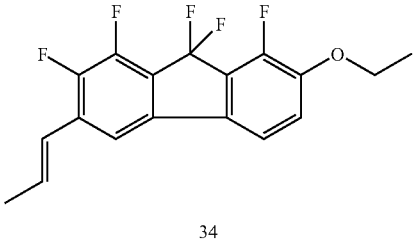
34

A solution of 1.7 g (15 mmol) of potassium tert-butoxide in 15 ml of THF is added under nitrogen to a suspension of 6.0 g (16.2 mmol) of ethyltris-triphenylphosphonium bromide in 30 ml of THF at 0° C. After 1 hour, the aldehyde 33, dissolved in 10 ml of THF, is added slowly, during which the batch temperature does not exceed 10° C. The batch is stirred overnight at room temperature, and water is subsequently added. The aqueous phase is extracted with MTB ether, and the organic phase is washed with sat. sodium chloride solution, dried over sodium sulfate and evaporated. The residue is passed through silica gel (MTB ether/n-heptane 1:15), giving 3.7 g (79%) of the olefin 34.

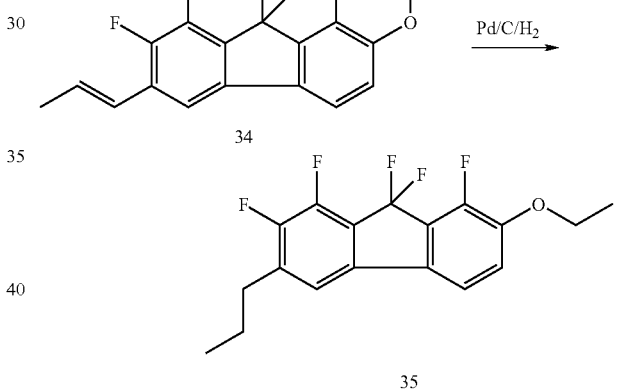

3.5 g (10.3 mmol) of the olefin 34 are dissolved in 40 ml of THF and hydrogenated on a palladium catalyst. The hydrogenation solution is evaporated. The residue obtained is passed through silica gel, giving 3.2 g (92%) of the pentafluorofluorene 35.

The following compounds according to the invention are obtained analogously to Example 641 using the corresponding precursors:

Examples 642 to 704

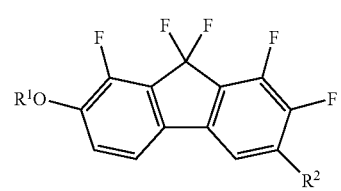

Examples 705 to 768

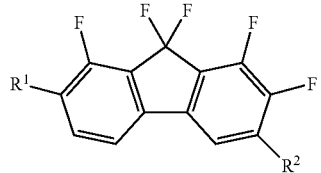

| Example No. | R$^1$ | R$^2$ |
|---|---|---|
| 641, 705 | C$_2$H$_5$ | n-C$_3$H$_7$ |
| 642, 706 | H | H |
| 643, 707 | H | CH$_3$ |
| 644, 708 | H | C$_2$H$_5$ |
| 645, 709 | H | n-C$_3$H$_7$ |
| 646, 710 | H | n-C$_4$H$_9$ |
| 647, 711 | H | n-C$_5$H$_{11}$ |
| 648, 712 | H | n-C$_6$H$_{13}$ |
| 649, 713 | H | n-C$_7$H$_{15}$ |
| 650, 714 | CH$_3$ | H |
| 651, 715 | CH$_3$ | CH$_3$ |
| 652, 716 | CH$_3$ | C$_2$H$_5$ |
| 653, 717 | CH$_3$ | n-C$_3$H$_7$ |
| 654, 718 | CH$_3$ | n-C$_4$H$_9$ |
| 655, 719 | CH$_3$ | n-C$_5$H$_{11}$ |
| 656, 720 | CH$_3$ | n-C$_6$H$_{13}$ |
| 657, 721 | CH$_3$ | n-C$_7$H$_{15}$ |
| 658, 722 | C$_2$H$_5$ | H |
| 659, 723 | C$_2$H$_5$ | CH$_3$ |
| 660, 724 | C$_2$H$_5$ | C$_2$H$_5$ |
| 661, 725 | C$_2$H$_5$ | n-C$_4$H$_9$ |
| 662, 726 | C$_2$H$_5$ | n-C$_5$H$_{11}$ |
| 663, 727 | C$_2$H$_5$ | n-C$_6$H$_{13}$ |
| 664, 728 | C$_2$H$_5$ | n-C$_7$H$_{15}$ |
| 665, 729 | n-C$_3$H$_7$ | H |
| 666, 730 | n-C$_3$H$_7$ | CH$_3$ |
| 667, 731 | n-C$_3$H$_7$ | C$_2$H$_5$ |
| 668, 732 | n-C$_3$H$_7$ | n-C$_3$H$_7$ |
| 669, 733 | n-C$_3$H$_7$ | n-C$_4$H$_9$ |
| 670, 734 | n-C$_3$H$_7$ | n-C$_5$H$_{11}$ |
| 671, 735 | n-C$_3$H$_7$ | n-C$_6$H$_{13}$ |
| 672, 736 | n-C$_3$H$_7$ | n-C$_7$H$_{15}$ |
| 673, 737 | n-C$_4$H$_9$ | H |
| 674, 738 | n-C$_4$H$_9$ | CH$_3$ |
| 675, 739 | n-C$_4$H$_9$ | C$_2$H$_5$ |
| 676, 740 | n-C$_4$H$_9$ | n-C$_3$H$_7$ |
| 677, 741 | n-C$_4$H$_9$ | n-C$_4$H$_9$ |
| 678, 742 | n-C$_4$H$_9$ | n-C$_5$H$_{11}$ |
| 679, 743 | n-C$_4$H$_9$ | n-C$_6$H$_{13}$ |
| 680, 744 | n-C$_4$H$_9$ | n-C$_7$H$_{15}$ |
| 681, 745 | n-C$_5$H$_{11}$ | H |
| 682, 746 | n-C$_5$H$_{11}$ | CH$_3$ |
| 683, 747 | n-C$_5$H$_{11}$ | C$_2$H$_5$ |
| 684, 748 | n-C$_5$H$_{11}$ | n-C$_3$H$_7$ |
| 685, 749 | n-C$_5$H$_{11}$ | n-C$_4$H$_9$ |
| 686, 750 | n-C$_5$H$_{11}$ | n-C$_5$H$_{11}$ |
| 687, 751 | n-C$_5$H$_{11}$ | n-C$_6$H$_{13}$ |
| 688, 752 | n-C$_5$H$_{11}$ | n-C$_7$H$_{15}$ |
| 689, 753 | n-C$_6$H$_{13}$ | H |
| 690, 754 | n-C$_6$H$_{13}$ | CH$_3$ |
| 691, 755 | n-C$_6$H$_{13}$ | C$_2$H$_5$ |
| 692, 756 | n-C$_6$H$_{13}$ | n-C$_3$H$_7$ |
| 693, 757 | n-C$_6$H$_{13}$ | n-C$_4$H$_9$ |
| 694, 758 | n-C$_6$H$_{13}$ | n-C$_5$H$_{11}$ |
| 695, 759 | n-C$_6$H$_{13}$ | n-C$_6$H$_{13}$ |
| 696, 760 | n-C$_6$H$_{13}$ | n-C$_7$H$_{15}$ |
| 697, 761 | n-C$_7$H$_{15}$ | H |
| 698, 762 | n-C$_7$H$_{15}$ | CH$_3$ |
| 699, 763 | n-C$_7$H$_{15}$ | C$_2$H$_5$ |
| 700, 764 | n-C$_7$H$_{15}$ | n-C$_3$H$_7$ |
| 701, 765 | n-C$_7$H$_{15}$ | n-C$_4$H$_9$ |
| 702, 766 | n-C$_7$H$_{15}$ | n-C$_5$H$_{11}$ |
| 703, 767 | n-C$_7$H$_{15}$ | n-C$_6$H$_{13}$ |
| 704, 768 | n-C$_7$H$_{15}$ | n-C$_7$H$_{15}$ |

The invention claimed is:

1. A compound of formula I:

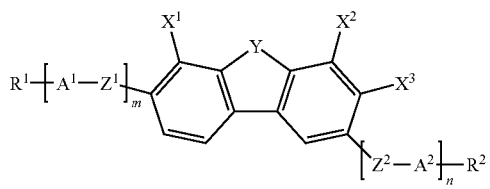

in which:

m and n are each, independently of one another, 0, 1, 2 or 3;

Y denotes O, S, S(O), SO$_2$, CH$_2$, CF$_2$, CCl$_2$, CHF, CHCl, CFCl, C(CF$_3$)$_2$, CHCF$_3$, C(CN)$_2$ or CHCN;

X$^1$, X$^2$ and X$^3$ each, independently of one another, denote H, halogen, CN, SCN, NCS or SF$_5$;

A$^1$ and A$^2$ each, independently of one another, denote 1,4-phenylene, in which =CH— may be replaced once or twice by =N— and which may be unsubstituted or mono- to tetrasubstituted, independently of one another, by —CN, —F, —Cl, —Br, —I, C$_1$-C$_6$-alkanyl which is unsubstituted or mono- or polysubstituted by fluorine and/or chlorine or by C$_1$-C$_6$-alkoxy which is unsubstituted or mono- or polysubstituted by fluorine and/or chlorine, 1,4-cyclohexylene, 1,4-cyclohexenylene or 1,4-cyclohexadienylene, in which —CH$_2$— may be replaced once or twice, independently of one another, by —O— or —S— in such a way that hetero atoms are not linked directly, and which may be unsubstituted or mono- or polysubstituted by —F, —Cl, —Br and/or —I;

Z$^1$ and Z$^2$ each, independently of one another, denote a single bond, a double bond, —CF$_2$O—, —OCF$_2$—, —CH$_2$CH$_2$—, —CF$_2$CF$_2$—, —CF$_2$CH$_2$—, —CH$_2$CF$_2$—, —CHF—CHF—, —C(O)O—, —OC(O)—, —CH$_2$O—, —OCH$_2$—, —CF=CH—, —CH=CF—, —CF=CF—, —CH=CH— or —C≡C—;

R$^1$ and R$^2$ denote an alkyl, alkoxy, alkenyl or alkynyl radical having 1 to 15 or 2 to 15 C atoms respectively which is unsubstituted, monosubstituted by —CN or —CF$_3$ or monosubstituted or polysubstituted by F, Cl, Br and/or I, where, in addition, one or more CH$_2$ groups in these radicals may each, independently of one another, be replaced by —O—, —S—, —SO$_2$—, —CO—, —COO—, —OCO— or —OCO—O— in such a way that hetero atoms are not linked directly, —F, —Cl, —Br, —I, —CN, —SCN, —NCS or —SF$_5$;

where

A$^1$, A$^2$, Z$^1$, Z$^2$, R$^1$ and R$^2$ may each have identical or different meanings if m or n is greater than 1; and where, in the case where m and n are both zero, R$^1$ and R$^2$ are each, independently of one another, an unbranched alkyl radical, alkoxy radical or alkenyl radical having 1 to 7 or 2 to 7 carbon atoms respectively.

2. A compound according to claim 1, wherein (m+n) is ≦3.

3. A compound according to claim 1, wherein Y=O or CF$_2$.

4. A compound of formula I

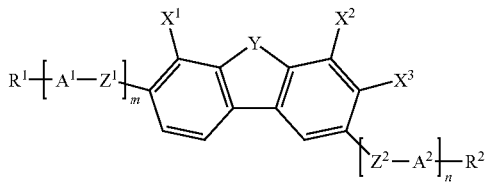

in which:
m and n are each, independently of one another, 0, 1, 2 or 3;
Y denotes O, S, S(O), SO₂, CH₂, CF₂, CCl₂, CHF, CHCl, CFCl, C(CF₃)₂, CHCF₃, C(CN)₂ or CHCN;
wherein at least two of the substituents $X^1$, $X^2$ and $X^3$ denote halogen and the third substituent denotes hydrogen or halogen,
$A^1$ and $A^2$ each, independently of one another, denote 1,4-phenylene, in which =CH— may be replaced once or twice by =N— and which may be unsubstituted or mono- to tetrasubstituted, independently of one another, by —CN, —F, —Cl, —Br, —I, $C_1$-$C_6$-alkanyl which is unsubstituted or mono- or polysubstituted by fluorine and/or chlorine or by $C_1$-$C_6$-alkoxy which is unsubstituted or mono- or polysubstituted by fluorine and/or chlorine, 1,4-cyclohexylene, 1,4-cyclohexenylene or 1,4-cyclohexadienylene, in which —CH₂— may be replaced once or twice, independently of one another, by —O— or —S— in such a way that hetero atoms are not linked directly, and which may be unsubstituted or mono-or polysubstituted by —F, —Cl, —Br and/or —I;
$Z^1$ and $Z^2$ each, independently of one another, denote a single bond, a double bond, —CF₂O—, —OCF₂—, —CH₂CH₂—, —CF₂CF₂—, —CF₂CH₂—, —CH₂CF₂—, —CHF—CHF—, —C(O)O—, —OC(O)—, —CH₂O—, —OCH₂—, —CF=CH—, —CH=CF—, —CF=CF—, —CH=CH— or —C≡C—;
$R^1$ and $R^2$ denote an alkyl, alkoxy, alkenyl or alkynyl radical having 1 to 15 or 2 to 15 C atoms respectively which is unsubstituted, monosubstituted by —CN or —CF₃ or monosubstituted or polysubstituted by F, Cl, Br and/or I, where, in addition, one or more CH₂ groups in these radicals may each, independently of one another, be replaced by —O—, —S—, —SO₂—, —CO—, —COO—, —OCO— or —OCO—O— in such a way that hetero atoms are not linked directly, —F, —Cl, —Br, —I, —CN, —SCN, —NCS or —SF₅;
where
$A^1$, $A^2$, $Z^1$, $Z^2$, $R^1$ and $R^2$ may each have identical or different meanings if m or n is greater than 1.

5. A compound according to claim 1, wherein $X^1$, $X^2$ and $X^3$ denote F.

6. A compound according to claim 1, wherein $Z^1$ and $Z^2$, independently of one another, are a single bond, —CF₂O—, —OCF₂—, —CF₂CF₂—, —CH=CH—, —CF=CH—, —CH=CF— or —CF=CF—.

7. A compound according to claim 1, wherein $A^1$ and $A^2$, independently of one another, are

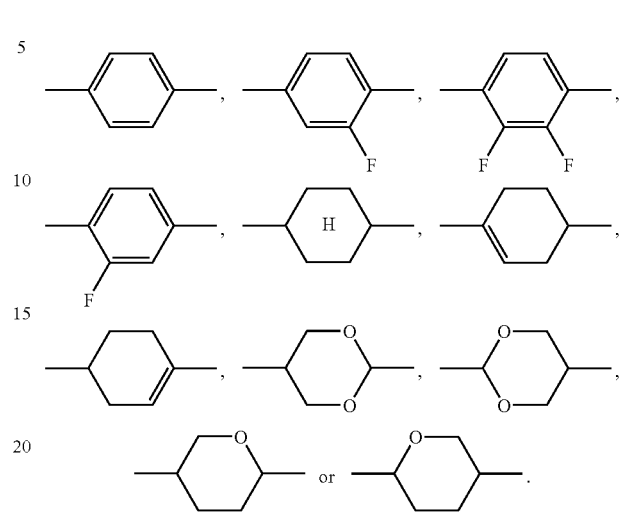

8. A compound according to claim 1, wherein $R^1$ and $R^2$ are each, independently of one another, an alkyl radical, alkoxy radical or alkenyl radical having 1 to 7 or 2 to 7 carbon atoms respectively, where each of these radicals is unsubstituted or monosubstituted or polysubstituted by halogen.

9. A compound according to claim 1, wherein
m and n are both zero; and
$R^1$ and $R^2$ are each, independently of one another, an unbranched alkyl radical, alkoxy radical or alkenyl radical having 1 to 7 or 2 to 7 carbon atoms respectively.

10. A compound according to at least one of claim 1, wherein m=1 and n=0;
$A^1$ is

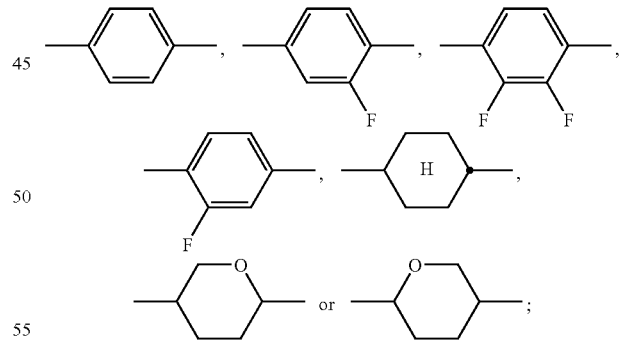

$Z^1$ is a single bond, —CF₂O—, —OCF₂—, —CF₂CF₂—, —CH=CH—, —CF=CH—, —CH=CF— or —CF=CF—;
$R^1$ is an alkanyl radical, alkoxy radical or alkenyl radical having 1 to 7 or 2 to 7 carbon atoms respectively; and
$R^2$ is hydrogen or an alkanyl radical, alkoxy radical or alkenyl radical having 1 to 7 or 2 to 7 carbon atoms respectively.

11. A compound according to claim 1, wherein
m and n are 1;
$A^1$ and $A^2$ are both

$Z^1$ and $Z^2$ are a single bond;
$R^1$ is an alkyl radical, alkoxy radical or alkenyl radical having 1 to 7 or 2 to 7 carbon atoms respectively; and
$R^2$ is an alkanyl radical, alkoxy radical or alkenyl radical having 1 to 7 or 2 to 7 carbon atoms respectively.

12. A liquid-crystalline medium comprising at least two liquid-crystalline compounds, wherein at least one compound is one according to claim 1.

13. An electro-optical display element containing a liquid-crystalline medium according to claim 12.

14. A compound of formula I:

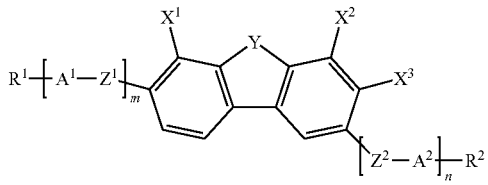

in which:
m and n are each, independently of one another, 0, 1, 2 or 3;
Y is $CF_2$;
$X^1$, $X^2$ and $X^3$ each, independently of one another, denote H, halogen, CN, SCN, NCS or $SF_5$; at least two of $X^1$, $X^2$ and $X^3$ are halogen,
$A^1$ and $A^2$ each, independently of one another, denote 1,4-phenylene, in which =CH— may be replaced once or twice by =N— and which may be unsubstituted or mono- to tetrasubstituted, independently of one another, by —CN, —F, —Cl, —Br, —I, $C_1$-$C_6$-alkanyl which is unsubstituted or mono- or polysubstituted by fluorine and/or chlorine or by $C_1$-$C_6$ -alkoxy which is unsubstituted or mono- or polysubstituted by fluorine and/or chlorine, 1,4-cyclohexylene, 1,4-cyclohexenylene or 1,4 -cyclohexadienylene, in which —$CH_2$— may be replaced once or twice, independently of one another, by —O— or —S— in such a way that hetero atoms are not linked directly, and which may be unsubstituted or mono- or polysubstituted by —F, —Cl, —Br and/or —I;
$Z^1$ and $Z^2$ each, independently of one another, denote a single bond, a double bond, —$CF_2$O—, —$OCF_2$—, —$CH_2CH_2$—, —$CF_2CF_2$—, —$CF_2CH_2$—, —$CH_2CF_2$—, —CHF—CHF—, —C(O)O—, —OC(O)—, —$CH_2$O—, —$OCH_2$—, —CF=CH—, —CH=CF—, —CF=CF—, —CH=CH— or —C≡C—;
$R^1$ and $R^2$ denote hydrogen, an alkyl, alkoxy, alkenyl or alkynyl radical having 1 to 15 or 2 to 15 C atoms respectively which is unsubstituted, monosubstituted by —CN or —$CF_3$ or monosubstituted or polysubstituted by F, Cl, Br and/or I, where, in addition, one or more $CH_2$ groups in these radicals may each, independently of one another, be replaced by —O—, —S—, —$SO_2$—, —CO—, —COO—, —OCO— or —OCO—O— in such a way that hetero atoms are not linked directly, —F, —Cl, —Br, —I, —CN, —SCN, —NCS or —$SF_5$;
where
$A^1$, $A^2$, $Z^1$, $Z^2$, $R^1$ and $R^2$ may each have identical or different meanings if m or n is greater than 1;
and where,
in the case where simultaneously n is 0, $X^1$ denotes F, $X^2$ denotes H or F and $X^3$ denotes H, $R^2$ then does not denote H.

15. A compound of formula I:

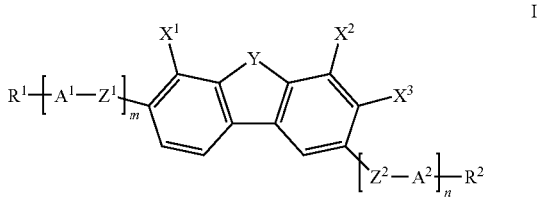

in which:
m and n are each, independently of one another, 0, 1, 2 or 3;
Y denotes O, S, S(O), $SO_2$, $CH_2$, $CF_2$, $CCl_2$, CHF, CHCl, CFCl, $C(CF_3)_2$, $CHCF_3$, $C(CN)_2$ or CHCN;
$X^1$, $X^2$ and $X^3$ each denote F;
$A^1$ and $A^2$ each, independently of one another, denote 1,4-phenylene, in which =CH— may be replaced once or twice by =N— and which may be unsubstituted or mono- to tetrasubstituted, independently of one another, by —CN, —F, —Cl, —Br, —I, $C_1$-$C_6$-alkanyl which is unsubstituted or mono- or polysubstituted by fluorine and/or chlorine or by $C_1$-$C_6$ -alkoxy which is unsubstituted or mono- or polysubstituted by fluorine and/or chlorine, 1,4-cyclohexylene, 1,4-cyclohexenylene or 1,4 -cyclohexadienylene, in which —$CH_2$— may be replaced once or twice, independently of one another, by —O— or —S— in such a way that hetero atoms are not linked directly, and which may be unsubstituted or mono- or polysubstituted by —F, —Cl, —Br and/or —I;
$Z^1$ and $Z^2$ each, independently of one another, denote a single bond, a double bond, —$CF_2$O—, —$OCF_2$—, —$CH_2CH_2$—, —$CF_2CF_2$—, —$CF_2CH_2$—, —$CH_2CF_2$—, —CHF—CHF—, —C(O)O—, —OC(O)—, —$CH_2$O—, —$OCH_2$—, —CF=CH—, —CH=CF—, —CF=CF—, —CH=CH— or
$R^1$ and $R^2$ denote hydrogen, an alkyl, alkoxy, alkenyl or alkynyl radical having 1 to 15 or 2 to 15 C atoms respectively which is unsubstituted, monosubstituted by —CN or —$CF_3$ or monosubstituted or polysubstituted by F, Cl, Br and/or I, where, in addition, one or more $CH_2$ groups in these radicals may each, independently of one another, be replaced by —O—, —S—, —$SO_2$—, —CO—, —COO—, —OCO— or —OCO—O— in such a way that hetero atoms are not linked directly, —F, —Cl, —Br, —I, —CN, —SCN, —NCS or —$SF_5$;
where
$A^1$, $A^2$, $Z^1$, $Z^2$, $R^1$ and $R^2$ may each have identical or different meanings if m or n is greater than 1.

* * * * *

UNITED STATES PATENT AND TRADEMARK OFFICE
CERTIFICATE OF CORRECTION

| | | |
|---|---|---|
| PATENT NO. | : 7,514,127 B2 | Page 1 of 1 |
| APPLICATION NO. | : 11/578376 | |
| DATED | : April 7, 2009 | |
| INVENTOR(S) | : Lars Lietzau et al. | |

It is certified that error appears in the above-identified patent and that said Letters Patent is hereby corrected as shown below:

Column 48, line 50 reads "—CH=CF—, —CF=CF—, —CH=CH— or" should read -- —CH=CF—, —CF=CF—, —CH=CH— or — C≡C— --

Signed and Sealed this

Twenty-eighth Day of July, 2009

JOHN DOLL
*Acting Director of the United States Patent and Trademark Office*